(12) United States Patent
Dorsch et al.

(10) Patent No.: US 10,179,777 B2
(45) Date of Patent: Jan. 15, 2019

(54) 3-(1H-BENZIMIDAZOL-2-YL)-1H-PYRIDIN-2-ONE DERIVATIVES

(71) Applicant: MERCK PATENT GMBH, Darmstadt (DE)

(72) Inventors: Dieter Dorsch, Ober-Ramstadt (DE); Alfred Jonczyk, Darmstadt (DE); Mireille Krier, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/566,933

(22) PCT Filed: Mar. 22, 2016

(86) PCT No.: PCT/EP2016/000495
§ 371 (c)(1),
(2) Date: Oct. 16, 2017

(87) PCT Pub. No.: WO2016/165808
PCT Pub. Date: Oct. 20, 2016

(65) Prior Publication Data
US 2018/0099947 A1 Apr. 12, 2018

(30) Foreign Application Priority Data
Apr. 16, 2015 (EP) ..................... 15001111

(51) Int. Cl.
| | | |
|---|---|---|
| *C07D 401/14* | (2006.01) | |
| *C07D 401/04* | (2006.01) | |
| *C07D 471/04* | (2006.01) | |
| *C07D 491/048* | (2006.01) | |
| *C07D 519/00* | (2006.01) | |
| *A61K 31/4184* | (2006.01) | |
| *A61K 31/4709* | (2006.01) | |
| *A61K 31/496* | (2006.01) | |
| *A61K 31/4995* | (2006.01) | |
| *A61K 31/5377* | (2006.01) | |
| *A61K 31/5513* | (2006.01) | |

(52) U.S. Cl.
CPC ........ *C07D 401/14* (2013.01); *A61K 31/4184* (2013.01); *A61K 31/4709* (2013.01); *A61K 31/496* (2013.01); *A61K 31/4995* (2013.01); *A61K 31/5377* (2013.01); *A61K 31/5513* (2013.01); *C07D 401/04* (2013.01); *C07D 471/04* (2013.01); *C07D 491/048* (2013.01); *C07D 519/00* (2013.01)

(58) Field of Classification Search
CPC ............ A61K 31/4184; A61K 31/4709; A61K 31/496; A61K 31/4995; A61K 31/5377; A61K 31/5513; C07D 471/04; C07D 491/048; C07D 519/00; C07D 401/14
USPC ........................................................ 514/218
See application file for complete search history.

(56) References Cited

U.S. PATENT DOCUMENTS

| | | |
|---|---|---|
| 8,629,147 B2 | 1/2014 | Anikin |
| 9,040,691 B2 | 5/2015 | Klar |
| 9,045,484 B2 | 6/2015 | Yu |
| 9,079,897 B2 | 7/2015 | Leblanc |
| 9,549,917 B2 | 1/2017 | McComas |
| 2016/0115167 A1 | 4/2016 | Yu |

FOREIGN PATENT DOCUMENTS

| | | |
|---|---|---|
| WO | 2002040467 A1 | 5/2002 |
| WO | 2007056155 A1 | 5/2007 |
| WO | 2009114180 A1 | 9/2009 |
| WO | 2009133070 A1 | 11/2009 |
| WO | 2013004551 A1 | 1/2013 |
| WO | 2013033901 A1 | 3/2013 |
| WO | 2014138088 A1 | 9/2014 |
| WO | 2016165808 A1 | 10/2016 |

OTHER PUBLICATIONS

International Search Report from PCT/EP2016/000495 dated Nov. 5, 2016.

*Primary Examiner* — Kahsay Habte
(74) *Attorney, Agent, or Firm* — Millen White Zelano and Branigan, PC; John Sopp

(57) ABSTRACT

Compounds of the formula I

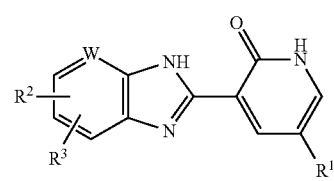

in which W, $R^1$, $R^2$ and $R^3$ have the meanings indicated in claim 1, are inhibitors of ALK1, AL2 and ALK5, and can be employed for the treatment of diseases such as cancer.

17 Claims, No Drawings

3-(1H-BENZIMIDAZOL-2-YL)-1H-PYRIDIN-2-ONE DERIVATIVES

BACKGROUND OF THE INVENTION

The invention had the object of finding novel compounds having valuable properties, in particular those which can be used for the preparation of medicaments.

The present invention relates to 3-(1H-benzimidazol-2-yl)-1H-pyridin-2-one derivatives which inhibit the activity of activin receptor like kinase (ALK-1; ALK-2, ALK-5). The compounds of this invention are therefore useful in treating diseases such as cancer.

The present invention also provides methods for preparing these compounds, pharmaceutical compositions comprising these compounds, and methods of treating diseases utilizing pharmaceutical compositions comprising these compounds.

ALK5 is a synonym of TGFbetaR1.

ALK1 inhibitors inhibit neovascularization. ALK1 inhibitors are useful in all diseases where neovascularization is involved, such as cancer, rheumatoid arthritis and diseases of the eye. They are useful for the treatment of age-related macular degeneration and similar ocular disorders (WO 2013/04551). ALK2 inhibitors are useful for the treatment of progressively debilitating muscoskeletal disease fibrodysplasia ossificans progressive (FOP). See C. E. Sanvitale et al PLOS ONE, April 2013, Volume 8, issue 4, e62721. Methods for evaluating responsiveness of a subject having cancer to treatment with an ALK1 antagonist are described in WO 2014/055869 A1. WO 2014/141118 A1 relates to imidazo[4,5-c]quinoline derivatives and their use in the treatment of diseases mediated by kinases such as PI3 kinase or ALK1. The compounds described in WO 2014/141118 A1 can be used for the treatment of cancer, inflammation, angiogensis related disorders and bacterial infections.

R. S. Bhatt et al. describe in Clin. Cancer Res. 2014; 20:2838-2845: Two ALK1 inhibitors have entered clinical trials, ACE-041 (dalantercept; Acceleron Pharma) and PF-03446962 (Pfizer).

M. Petersen et al. describe in Kidney International (2008) 73, 705-715 the use of GW788388, an inhibitor of the TGF-β type I and II receptor kinases, for the treatment of renal fibrosis.

WO 2014/151871 A2 discloses pyrimidine derivatives as ALK2 inhibitors for the treatment of cancer, such as a myeloproliferative disorder, a lymphoma or a solid tumor, moreover for the treatment of anemia of chronic disease, anemia of chronic inflammation, anemia of cancer or fibrodysplasia ossificans progressive.

Members of the transforming growth factor-β (TGF-β) superfamily, including TGF-β, activin, nodal, and bone morphogenetic proteins (BMPs), are multifunctional cytokines that regulate a wide range of cellular responses, including cell proliferation, differentiation, adhesion, migration, and apoptosis.[1,2] TGF-β and related proteins transduce signals through two distinct serine/threonine kinase receptors, termed type I and type II.[3,4] The type II receptors are the primary ligand binding receptors at the cell surface and contain constitutively active kinases, which phosphorylate corresponding type I receptors. Seven type I receptors termed activin receptor-like kinase (ALK) 1 through 7 have been identified in mammals. ALK-4, ALK-5, and ALK-7 are structurally highly related to each other and transduce similar, though not identical, intracellular signals.[5] TGF-β and activin bind to ALK-5 (type I TGF-β receptor; TβR-I) and ALK-4 (type IB activin receptor; ActR-IB), respectively. Signals for nodal proteins are transduced by ALK-4 as well as ALK-7.[6] In contrast, ALK-1, -2, -3 and -6 transmit signals similar to each other's. BMPs bind to ALK-2, ALK-3 (type IA BMP receptor; BMPR-IA), and ALK-6 (type IB BMP receptor; BMPR-IB), whereas ALK-1 is highly expressed in endothelial cells and binds to TGF-β in these cells.[7]

Upon activation by type II receptors, type I receptor ALKs transduce intracellular signals through various proteins, of which Smad proteins are the major signaling molecules for TGF-β superfamily proteins.[3,5] Eight different Smad proteins have been identified in mammals, and are classified into three groups: receptor-regulated Smads (R-Smads), common-partner Smads (Co-Smads), and inhibitory Smads (I-Smads). Smad2 and Smad3 are R-Smads activated by TGF-β/activin/nodal receptors ALK-4, -5, and -7, whereas Smad1, Smad5, and Smad8 are BMP-specific R-Smads.[5] Smad4 is the Co-Smad shared by signaling pathways for TGF-β and activin and those for BMPs. Smad6 and Smad7 are I-Smads in mammals; Smad6 preferentially suppresses BMP signaling, whereas Smad7 inhibits both BMP and TGF-β signaling.

The roles of TGF-β in cancer biology are complex; TGF-β can suppress or promote tumor growth depending on the type of cancer. The ability of TGF-β to potently inhibit the proliferation of epithelial, endothelial, and hematopoietic cell lineages is central to its tumor-suppressive effects. However, as tumors evolve, they often become refractory to TGF-β-mediated growth inhibition and overexpress TGF-β, which induces epithelial-to-mesenchymal transition (EMT) of tumor cells and facilitates immunosuppression, extracellular matrix deposition, and angiogenesis. It was recently reported that inhibition of autocrine TGF-β signaling in carcinoma cells reduces cell invasiveness and tumor metastasis, and that these effects of TGF-β are closely associated with the ability of TGF-β to induce EMT and stimulate cell migration.[8,9] The TGF-β signaling pathway has correspondingly become an attractive target for drug development in the field of oncology.[10,11]

G. J. Inman et al., Molecular Pharmacology Jul. 1, 2002 vol. 62 no. 1, 65-74, characterized a small molecule inhibitor (SB-431542) that was identified as an inhibitor of activin receptor-like kinase (ALK)5 (the TGF-β type I receptor). They demonstrated that it inhibits ALK5 and also the activin type I receptor ALK4 and the nodal type I receptor ALK7, which are very highly related to ALK5 in their kinase domains.

REFERENCES

1
Derynck R, Akhurst R J, Balmain A. TGF-β signaling in tumor suppression and cancer progression. *Nat Genet* 2001; 29: 117-29.

2
Miyazono K, Suzuki H, Imamura T. Regulation of TGF-β signaling and its roles in progression of tumors. *Cancer Sci* 2003; 94:230-34.

3
Heldin C H, Miyazono K, Ten Dijke P. TGF-β signaling from cell membrane to nucleus through SMAD proteins. *Nature* 1997; 390:465-71.

4
Shi Y, Massagué J. Mechanisms of TGF-β signaling from cell membrane to the nucleus. *Cell* 2003; 113: 685-700.

5 Miyazawa K, Shinozaki M, Hara T, Furuya T, Miyazono K. Two major Smad pathways in TGF-β superfamily signaling. *Genes Cells* 2002; 7: 1191-204. Direct Link:

6 Reissmann E, Jornvall H, Blokzijl A et al. The orphan receptor ALK7 and the activin receptor ALK4 mediate signaling by nodal proteins during vertebrate development. *Genes Dev* 2001; 15: 2010-22.

7 Oh S P, Seki T, Goss K A et al. Activin receptor-like kinase 1 modulates transforming growth factor-β 1 signaling in the regulation of angiogenesis. *Proc Natl Acad Sci USA* 2000; 97: 2626-31.

8 Bandyopadhyay A, Zhu Y, Cibull M L, Bao L, Chen C, Sun L. A soluble transforming growth factor β type III receptor suppresses tumorigenicity and metastasis of human breast cancer MDA-MB-231 cells. *Cancer Res* 1999; 59: 5041-6.

9 Oft M, Heider K H, Beug H. TGF-β signaling is necessary for carcinoma cell invasiveness and metastasis. *Curr Biol* 1998; 8:1243-52.

10 Dumont N, Arteaga C L. Targeting the TGF β signaling network in human neoplasia. *Cancer Cell* 2003; 3: 531-6.

11 Yingling J M, Blanchard K L, Sawyer J S. Development of TGF-β signalling inhibitors for cancer therapy. *Nat Rev Drug Discov* 2004; 3:1011-22.

Pharmacologic inhibitors of ALK1 have recently been developed. ALK1 has been described as an emerging target for antiangiogenic therapy of cancer by S. I. Cunha et al. http://www.bloodjournal.org/content/117/26/6999.

The use of ALK1 inhibitors for treating angiogenesis-related ocular diseases, such as age-related macular degeneration (AMD), choroidal neovascularization (CNV), diabetic retinopathy and diabetic macula edema (DME) has been described in WO 2013/004551 A1.

ALK2 inhibitors are useful for the treatment of progressively debilitating muscoskeletal disease fibrodysplasia ossificans progressive (FOP). See C. E. Sanvitale et al PLOS ONE, April 2013, Volume 8, issue 4, e62721. All known ALK1 inhibitors are also ALK2 inhibitors and vice versa.

WO 2012/104007 discloses compounds which exhibit TGFβ receptor I kinase-inhibiting properties.

A number of diseases have been associated with TGF-β1 overproduction. Inhibitors of the intracellular TGF-β signaling pathway are suitable treatments for fibroproliferative diseases. Specifically, fibroproliferative diseases include kidney disorders associated with unregulated TGF-β activity and excessive fibrosis including glomerulonephritis (GN), such as mesangial proliferative GN, immune GN and crescentic GN. Other renal conditions include diabetic nephropathy, renal interstitial fibrosis, renal fibrosis in transplant patients receiving cyclosporin, and HIV-associated nephropathy. Collagen vascular disorders include progressive systemic sclerosis, polymyositis, sclerodermatitis, dermatomyositis, eosinophilic fasciitis, morphea, or those associated with the occurrence of Raynaud's syndrome. Lung fibroses resulting from excessive TGF-β activity include adult respiratory distress syndrome, idiopathic pulmonary fibrosis, and interstitial pulmonary fibrosis often associated with autoimmune disorders, such as systemic lupus erythematosus and scleroderma titis, chemical contact or allergies. Another autoimmune disorder associated with fibroproliferative characteristics is rheumatoid arthritis.

Eye diseases associated with a fibroproliferative condition include proliferative vitreoretinopathy occurring during retinal reattachment surgery, cataract extraction with intraocular lens implantation, and post-glaucoma drainage surgery and are associated with TGF-β1 overproduction.

It has been found that the compounds according to the invention and salts thereof have very valuable pharmacological properties while being well tolerated.

The present invention specifically relates to compounds of the formula I which inhibit ALK1 (ACVRL1), ALK2 (ACVR1) and/or ALK5 (TGFβR1), to compositions which comprise these compounds, and to processes for the use thereof for the treatment of ALK1-, ALK2-, and/or ALK5-induced diseases and complaints. Moreover, compounds of formula I inhibit BMP-induced phosphorylation of SMAD1/5/8.

All known ALK1 inhibitors are also ALK2 inhibitors and vice versa. No real selective ALK1 or ALK2 inhibitors are known.

Compounds according to the invention also inhibit both ALK1 and ALK2.

The compounds of the formula I can furthermore be used for the isolation and investigation of the activity or expression of ALKs. In addition, they are particularly suitable for use in diagnostic methods for diseases in connection with unregulated or disturbed ALK1, ALK2 and/or ALK5 activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Other benzimidazolyl derivatives compounds have been described as tyrosine kinase modulators in WO 2007/056155 A1. Heterocyclic substituted benzofuran derivatives for the treatment of viral diseases have been described in WO 2013/033901 A1. Other heterocyclic compounds as ALK1 inhibitors for treating angiogenesis-related disorders have been described in WO 2013/004551 A1.

Other bicyclic heterocylic compounds are described in WO 2009/114180 and WO 2014/138088 as inhibitors of ALK2 and of BMP-induced phosphorylation of SMAD1/5/8.

SUMMARY OF THE INVENTION

The invention relates to compounds of the formula I in which

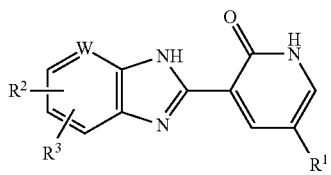

I $R^1$ denotes Ar or Het,
$R^2$ denotes H, A, Hal, CN, NO$_2$, OR$^4$, COOR$^4$, CO(R$^4$)$_2$, CONR$^4$[C(R$^4$)$_2$]$_m$N(R$^4$)$_2$, —[C(R$^4$)$_2$]$_n$NR$^4$COA, —[C(R$^4$)$_2$]$_n$NR$^4$CO[C(R$^4$)$_2$]$_n$Het$^1$, —[C(R$^4$)$_2$]$_n$N(R$^4$)$_2$, —[C(R$^4$)$_2$]$_n$Het$^1$, O[C(R$^4$)$_2$]$_n$N(R$^4$)$_2$, O[C(R$^4$)$_2$]$_m$Het$^1$, —NR$^4$[C(R$^4$)$_2$]$_m$N(R$^4$)$_2$ or —NR$^4$[C(R$^4$)$_2$]$_n$Het$^1$,
$R^3$ denotes H, A, Hal or OR$^4$,
$R^4$ denotes H or A',
W denotes CH or N,
A denotes unbranched or branched alkyl having 1-6 C-atoms, in which 1-7 H atoms may be replaced by OH, F, Cl and/or Br and/or in which one or two CH$_2$ groups may be replaced by O, NH, S, SO, SO$_2$ and/or CH=CH groups, or cyclic alkyl having 3-7 C atoms,
A' denotes unbranched or branched alkyl having 1-4 C-atoms,
Ar denotes phenyl or naphthyl, which is unsubstituted or mono-, di- or trisubstituted by Hal, A, [C(R$^4$)$_2$]$_n$OR$^4$ and/or [C(R$^4$)$_2$]$_n$N(R$^4$)$_2$,
Het denotes pyridyl, quinolyl, [1,8]-naphthyridinyl, pyrazolyl, pyrimidinyl, indolyl, dihydro-indolyl, 1H-pyrrolo[2,3-b]pyridyl, furyl, pyrazolo[1,5-a]pyridinyl or furo[3,2-b]pyridinyl, which may be unsubstituted or mono- or disubstituted by Hal, A, [C(R$^4$)$_2$]$_n$OR$^4$ and/or [C(R$^4$)$_2$]$_n$N(R$^4$)$_2$,
Het$^1$ denotes piperazinyl, pyridyl, piperidinyl, pyrazolyl, morpholinyl, imidazolyl, 3,8-diaza-bicyclo[3.2.1]octyl, or [1,4]-diazepanyl, which is unsubstituted or mono- or disubstituted by A, OR$^4$, N(R$^4$)$_2$, Hal and/or =O (carbonyl oxygen),
Hal denotes F, Cl, Br or I,
n denotes 0, 1, 2 or 3,
m denotes 1, 2, 3 or 4,
and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically acceptable salts, solvates, tautomers and stereoisomers thereof, characterised in that a) a compound of the formula II

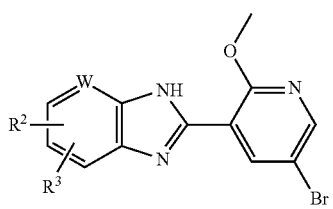

in which W, $R^2$ and $R^3$ have the meanings indicated in claim 1, is reacted in a Suzuki-type coupling, with a compound of formula III

L-$R^1$    III in which $R^1$ has the meanings indicated in claim 1, and L denotes a boronic acid or a boronic acid ester group, to give a compound of formula IV

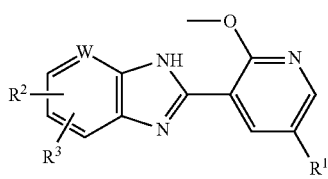

in which W, $R^1$, $R^2$ and $R^3$ have the meanings indicated in claim 1, which subsequently is reacted with a mineral acid, or b) that it is liberated from one of its functional derivatives by treatment with a solvolysing or hydrolysing agent, or c) a radical $R^2$ is converted into another radical $R^2$ by acylating or alkylating an amino group, and/or a base or acid of the formula I is converted into one of its salts.

Above and below, the radicals W, $R^1$, $R^2$ and $R^3$ have the meanings indicated for the formula I, unless explicitly stated otherwise.

A denotes alkyl, this is unbranched (linear) or branched, and has 1, 2, 3, 4, 5, 6, 7 or 8 C atoms. A preferably denotes methyl, ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Cyclic alkyl preferably denotes cyclopropyl, cyclobutyl, cyclopentyl, cyclohexyl Moreover, A denotes preferably $CH_2OCH_3$, $CH_2CH_2OH$ or $CH_2CH_2OCH_3$. A' denotes alkyl, this is unbranched (linear) or branched, and has 1, 2, 3 or 4 C atoms. A' preferably denotes methyl, ethyl, propyl, isopropyl, butyl, isobutyl, sec-butyl or tert-butyl.

$R^2$ preferably denotes H, A, Hal, CN, $OR^4$, $COOR^4$, $CONR^4[C(R^4)_2]_mN(R^4)_2$, —$[C(R^4)_2]_nNR^4COA$, —$[C(R^4)_2]_nNR^4CO[C(R^4)_2]_nHet^1$, —$[C(R^4)_2]_nN(R^4)_2$, —$[C(R^4)_2]_nHet^1$, $O[C(R^4)_2]_mHet^1$ or —$NR^4[C(R^4)_2]_nHet^1$.

$R^3$ preferably denotes H or $OR^4$.

$R^4$ preferably denotes H or methyl.

W preferably denotes CH.

Ar preferably denotes phenyl, which is mono-, di- or trisubstituted by Hal, A, $[C(R^4)_2]_nOR^4$ and/or $[C(R^4)_2]_nN(R^4)_2$.

Het preferably denotes pyridyl, quinolyl, [1,8]-naphthyridinyl, pyrazolyl, pyrimidinyl, indolyl, dihydro-indolyl, 1H-pyrrolo[2,3-b]pyridyl, furyl, pyrazolo[1,5-a]pyridinyl or furo[3,2-b]pyridinyl, which may be unsubstituted or monosubstituted by A.

$Het^1$ preferably denotes piperazinyl, pyridyl, piperidinyl, pyrazolyl, morpholinyl, imidazolyl, 3,8-diaza-bicyclo[3.2.1]octyl, or [1,4]-diazepanyl, which is unsubstituted or mono- or disubstituted by A, $OR^4$ and/or $N(R^4)_2$.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which in Ia $R^2$ denotes H, A, Hal, CN, $OR^4$, $COOR^4$, $CONR^4$ $[C(R^4)_2]_mN(R^4)_2$, —$[C(R^4)_2]_nNR^4COA$, —$[C(R^4)_2]_n$ $NR^4CO[C(R^4)_2]_nHet^1$, —$[C(R^4)_2]_nN(R^4)_2$, —$[C(R^4)_2]_nHet^1$, $O[C(R^4)_2]_mHet^1$ or —$NR^4[C(R^4)_2]_nHet^1$;

in Ib $R^3$ denotes H or $OR^4$;

in Ic $R^4$ denotes H or methyl;

in Id W denotes CH;

in Ie A denotes unbranched or branched alkyl having 1-6 C-atoms;

in If A' denotes unbranched or branched alkyl having 1-4 C-atoms;

in Ig Ar denotes phenyl, which is mono-, di- or trisubstituted by Hal, A, $[C(R^4)_2]_nOR^4$ and/or $[C(R^4)_2]_nN(R^4)_2$;

in Ih Het denotes pyridyl, quinolyl, [1,8]-naphthyridinyl, pyrazolyl, pyrimidinyl, indolyl, dihydro-indolyl, 1H-pyrrolo[2,3-b]pyridyl, furyl, pyrazolo[1,5-a]pyridinyl or furo[3,2-b]pyridinyl, which may be unsubstituted or monosubstituted by A;

in Ii $Het^1$ denotes piperazinyl, pyridyl, piperidinyl, pyrazolyl, morpholinyl, imidazolyl, 3,8-diaza-bicyclo[3.2.1]octyl, or [1,4]-diazepanyl, which is unsubstituted or mono- or disubstituted by A, $OR^4$ and/or $N(R^4)_2$;

in Ij $R^1$ denotes Ar or Het,
$R^2$ denotes H, A, Hal, CN, $OR^4$, $COOR^4$, $ONR^4[C(R^4)_2]_m$ $N(R^4)_2$, —$[C(R^4)_2]_nNR^4COA$, —$[C(R^4)_2]_nNR^4CO[C(R^4)_2]_nHet^1$, —$[C(R^4)_2]_nN(R^4)_2$, —$[C(R^4)_2]_nHet^1$, $O[C(R^4)_2]_mHet^1$ or —$NR^4[C(R^4)_2]_nHet^1$, $R^3$ denotes H or $OR^4$, $R^4$ denotes H or A', W denotes CH, A denotes unbranched or branched alkyl having 1-6 C-atoms, A' denotes H or methyl, Ar denotes phenyl, which is mono-, di- or trisubstituted by Hal, A, [C(R⁴)₂]ₙOR⁴ and/or [C(R⁴)₂]ₙN(R⁴)₂, Het denotes pyridyl, quinolyl, [1,8]-naphthyridinyl, pyrazolyl, pyrimidinyl, indolyl, dihydro-indolyl, 1H-pyrrolo[2,3-b]pyridyl, furyl, pyrazolo[1,5-a]pyridinyl or furo[3,2-b]pyridinyl, which may be unsubstituted or monosubstituted by A, Het¹ denotes piperazinyl, pyridyl, piperidinyl, pyrazolyl, morpholinyl, imidazolyl, 3,8-diaza-bicyclo[3.2.1]octyl, or [1,4]-diazepanyl, which is unsubstituted or mono- or disubstituted by A, OR⁴ and/or N(R⁴)₂, Hal denotes F, Cl, Br or I, n denotes 0, 1, 2 or 3, m denotes 1, 2, 3 or 4, and pharmaceutically acceptable salts, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds of the formula II and III are generally known. If they are novel, however, they can be prepared by methods known per se.

Compounds of the formula I can preferably be obtained by reacting in a first step the compound of the formula II with a compound of the formula III to give a compound of formula IV.

In the compounds of the formula III, L preferably denotes

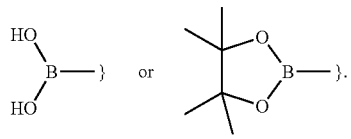

Compounds of formula I can be synthesized by a coupling reaction ("Suzuki coupling") between the bromo-heterocycles of formula H and an aryl boronate or boronic acid of formula III giving a compound of formula IV.

This coupling is generally carried out at elevated temperature using a palladium catalyst, a base and an inert solvent. An overview of catalysts and reaction conditions can be found in the literature [see, for instance, S. Kotha et al., Tetrahedron 2002, 58, 9633-9695; T. E. Barder et al., J. Am. Chem. Soc. 2005, 127, 4685-4696]. The preferred catalyst in this reaction is tetrakis(triphenylphosphine)-palladium(0). The preferred base is sodium carbonate employed as an aqueous solution. The reaction is carried out in organic solvents that are inert under the reaction conditions, such as 1,4-dioxane, acetonitrile, N,N-dimethylformamide (DMF) or dimethylsulfoxide (DMSO), or in water or in mixtures of these solvents. Preferably, the reaction is carried out in a mixture of 1,4-dioxane and water or acetonitrile and water. The reaction is generally performed at temperatures between +100° C. and +250° C., preferably at +110° C. to +150° C. Heating is preferably effected by a singlemode microwave device. The reactions are usually run under an inert gas atmosphere, preferably under argon.

In a second step the compound of the formula IV is reacted with a mineral acid, such HCl.

It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The alkylation also can be performed under reducing alkylating conditions, such as the use of HCHO and NaBH₃CN.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an aminoprotecting group instead of an H atom bonded to an N atom, for example those which conform to the formula I, but contain an NHR' group (in which R' is an aminoprotecting group, for example BOC or CBZ) instead of an NH₂ group.

Preference is furthermore given to starting materials which carry a hydroxyl-protecting group instead of the H atom of a hydroxyl group, for example those which conform to the formula I, but contain an R"O-phenyl group (in which R" is a hydroxyl protecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "aminoprotecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the aminoprotecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred aminoprotecting groups are BOC and Mtr, furthermore CBZ, Fmoc, benzyl and acetyl.

The term "hydroxyl protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl protecting groups are not crucial since they are removed again after the desired chemical reaction or reaction sequence; preference is given to groups having 1-20, in particular 1-10, carbon atoms. Examples of hydroxyl protecting groups are, inter alia, tert-butoxycarbonyl, benzyl, p-nitrobenzoyl, p-toluenesulfonyl, tert-butyl and acetyl, where benzyl and tert-butyl are particularly preferred.

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

The azaindole group preferably is protected during the reaction steps by means of a phenylsulfonyl group. This group preferably is cleaved off with $Cs_2CO_3$ in $CF_3CH_2OH$/THF.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methyl-glutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t1/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and pharmaceutically salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, tautomers and stereoisomers thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base.

Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, tautomers and stereoisomers thereof, including mixtures thereof in all ratios, and at least one further medicament active ingredient.

The invention also relates to a set (kit) consisting of separate packs of
 (a) an effective amount of a compound of the formula I and/or pharmaceutically acceptable salts, tautomers and stereoisomers thereof, including mixtures thereof in all ratios, and
 (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, tautomers and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula (I) is an amount that inhibits a tankyrase in a cell, such as, for example, in vitro or in vivo. In some embodiments, the effective amount of the compound of formula (I) inhibits tankyrase in a cell by 10%, 20%, 30%, 40%, 50%, 60%, 70%, 80%, 90% or 99%, compared to the activity of tankyrase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of cancer, for treating angiogenesis-related ocular diseases, such as age-related macular degeneration (AMD), choroidal neovascularization (CNV), diabetic retinopathy and diabetic macula edema (DME).

The present invention encompasses the use of the compounds of the formula I and/or pharmaceutically acceptable salts, tautomers and stereoisomers thereof for the preparation of a medicament for the treatment or prevention of cancer, for treating angiogenesis-related ocular diseases, such as age-related macular degeneration (AMD), choroidal neovascularization (CNV), diabetic retinopathy and diabetic macula edema (DME).

Moreover, the present invention encompasses the use of the compounds of the formula I and/or pharmaceutically acceptable salts, tautomers and stereoisomers thereof for the preparation of a medicament for the treatment or prevention of cancer, age-related macular degeneration (AMD), choroidal neovascularization (CNV), diabetic retinopathy, diabetic macula edema (DME), fibrodysplasia ossificans progressive, inflammation, angiogenesis related disorders and bacterial infections.

Moreover, the present invention encompasses the use of the compounds of the formula I and/or pharmaceutically acceptable salts, tautomers and stereoisomers thereof for the preparation of a medicament for the treatment or prevention of fibrodysplasia ossificans progressive, inflammation, angiogenesis related disorders and bacterial infections.

Also encompassed is the use of the compounds of the formula I and/or pharmaceutically acceptable salts, tautomers and stereoisomers thereof for the preparation of a medicament for the treatment or prevention of a ALK1-, ALK2- and/or ALK5-induced disease or a ALK1-, ALK2- and/or ALK5-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The expression "ALK1-, ALK2- and/or ALK5-induced diseases or conditions" refers to pathological conditions that depend on the activity of ALK1, ALK2, ALK5. Diseases associated with ALK1, ALK2, ALK5 activity include cancer, angiogenesis-related ocular diseases, such as age-related macular degeneration (AMD), choroidal neovascularization (CNV), diabetic retinopathy and diabetic macula edema (DME).

The present invention specifically relates to compounds of the formula I and pharmaceutically acceptable salts, tautomers and stereoisomers thereof, including mixtures thereof in all ratios,
for the use for the treatment of diseases in which the inhibition, regulation and/or modulation inhibition of ALK1, ALK2 and/or ALK5 plays a role.

The present invention specifically relates to compounds of the formula I and pharmaceutically acceptable salts, tautomers and stereoisomers thereof, including mixtures thereof in all ratios, for the use for the inhibition of ALK1, ALK2 and/or ALK5.

The present invention specifically relates to compounds of the formula I and pharmaceutically acceptable salts, tautomers and stereoisomers thereof, including mixtures thereof in all ratios, for the use for the treatment of cancer, angiogenesis-related ocular diseases, such as age-related macular degeneration (AMD), choroidal neovascularization (CNV), diabetic retinopathy and diabetic macula edema (DME).

Moreover, the present invention specifically relates to compounds of the formula I and pharmaceutically acceptable salts, solvates, tautomers and stereoisomers thereof, including mixtures thereof in all ratios, for the use for the treatment and/or prevention of cancer, age-related macular degeneration (AMD), choroidal neovascularization (CNV), diabetic retinopathy, diabetic macula edema (DME), fibrodysplasia ossificans progressive, inflammation, angiogenesis related disorders and bacterial infections.

The present invention specifically relates to methods for treating or preventing cancer, angiogenesis-related ocular diseases, such as age-related macular degeneration (AMD), choroidal neovascularization (CNV), diabetic retinopathy and diabetic macula edema (DME), comprising administering to a subject in need thereof an effective amount of a compound of formula I or a pharmaceutically acceptable salt, tautomer, stereoisomer or solvate thereof.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents.

As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA Altering Agents such as amrubicin, bisantrene, decitabine, mitoxantrone, procarbazine, trabectedin, clofarabine; amsacrine, brostallicin, pixantrone, laromustine[1,3];

Topoisomerase Inhibitors such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine; fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin; aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase Inhibitors such as aminoglutethimide, anastrozole, exemestane, fadrozole, letrozole, testolactone; formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3]; porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1]Prop. INN (Proposed International Nonproprietary Name)
[2]Rec. INN (Recommended International Nonproprietary Names)
[3]USAN (United States Adopted Name)
[4]no INN.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethyl-carbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethylammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

$^1$H NMR was recorded on Bruker DPX-300, DRX-400, AVII-400 or on a 500 MHz spectrometer, using residual signal of deuterated solvent as internal reference. Chemical shifts (δ) are reported in ppm relative to the residual solvent signal (δ=2.49 ppm for $^1$H NMR in DMSO-$d_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

HPLC/MS Conditions:
HPLC/MS: Agilent 1200/6100
eluent A: water+0.05% formic acid
eluent B: acetonitrile+0.04% formic acid
column: Kinetex XB-C18; 2.6 μm; 50-4.6 mm
flow rate: 2.5 ml/min
gradient: 0%→100% B: 0.0→1.4 min|100% B: 1.4→2.0 min
UV detection: 220 nm
MS detection: 65-800 amu positive Assays The protein sequences of the kinases targeted and accompanying information are described in publically available data base http://www.uniprot.org/uniprot/for ALK1 www.uniprot.org/uniprot/P37023, for ALK2 www.uniprot.org/uniprot/Q04771 and for ALK5 www.uniprot.org/uniprot/P36897. IC50 determination of the novel inhibitors described was performed at Reaction Biology Corp., Malvern, Pa., USA, with assay conditions open to public at www.reactionbiology.com/webapps/site/KinaseDetail.aspx?page=Kinases&id=1, and www.reactionbiology.com/webapps/site/Kinase Assay Protocol.aspx. In addition, they were specified previously in Anastassiadis et al. Nat. Biotechnol. 29(11): 1039-1045. doi:10.1038/nbt.2017.

A1) ALK1 Kinase Inhibition Assay was performed with N-terminally GST-modified kinase domain ACVRL1 (139-503) and 20 mg/ml Casein as substrate in reaction buffer of 20 mM HEPES pH 7.5, 10 mM MgCl2, 1 mM EGTA, 0.02% Brij, 0.02 mg/ml BSA, 0.1 mM Na3VO4, 2 mM DTT, 1% DMSO. Compounds are dissolved in DMSO to give 10 mM stock solution and were delivered into the reaction at concentrations diluted from 10 μM to 0.1 nM followed about 20 min later by addition of a mixture of ATP (Sigma, St. Louis, Mo., USA) and 33P-ATP (Perkin Elmer, Waltham, Mass., USA) to a final concentration of 100 μM (Km ATP). Reactions were carried out at ambient temperature for 120 min, followed by spotting of the reactions onto P81 ion exchange filter paper (Whatman Inc., Picataway, N.J., USA). Unbound phosphate was removed by extensive washing of filters in 0.75% phosphoric acid. After subtraction of background derived from control reactions without enzyme activity, kinase activity data was expressed as the percent remaining kinase activity in test samples compared to vehicle (DMSO) reactions. IC50 values and curve fits were obtained using Prism (GraphPad Software).

A2) ALK2 Kinase Inhibition Assay was performed similar to procedure A1 with N-terminally GST-modified kinase domain ACVR1(145-509) and 1 mg/ml Casein as substrate in reaction buffer of 20 mM HEPES pH 7.5, 10 mM MgCl2, 1 mM EGTA, 0.02% Brij, 0.02 mg/ml BSA, 0.1 mM Na3VO4, 2 mM DTT, 1% DMSO. Compounds are dissolved in DMSO to give 10 mM stock solution and were delivered into the reaction at concentrations diluted from 10 μM to 0.1 nM followed about 20 min later by addition of a mixture of ATP (Sigma, St. Louis, Mo., USA) and 33P-ATP (Perkin Elmer, Waltham, Mass., USA) to a final concentration of 20 μM (Km ATP). Reactions were carried out at ambient temperature for 120 min, followed by spotting of the reactions onto P81 ion exchange filter paper (Whatman Inc., Picataway, N.J., USA). Unbound phosphate was removed by extensive washing of filters in 0.75% phosphoric acid. After subtraction of background derived from control reactions without enzyme activity, kinase activity data was expressed as the percent remaining kinase activity in test samples compared to vehicle (DMSO) reactions. IC50 values and curve fits were obtained using Prism (GraphPad Software).

A3) ALK5 Kinase Inhibition Assay Was Performed Similar to Procedures A1 and A2 Using GST-Modified TGFBR1 (200-503) and 1 mg/ml Casein as Substrate at 200 μM ATP.

Smad 1/5

In vitro cell-based Immunofluorescence-Assay for identification of inhibitors of ALK1-mediated SMAD1/5 phosphorylation in HUVEC cells:

ALK1 is a type I cell-surface receptor for the TGF-β superfamily of ligands. In adults ALK1 is mainly expressed on activated endothelial cells, e.g. during wound healing or in tumor angiogenesis. BMP9 and BMP10 are high affinity ligands for ALK1.

BMP9 and BMP10 binding leads to the phosphorylation of so-called Smad1 at Ser463 and Ser465 in the carboxy-terminal motif SSXS, as well as Smad5 and Smad8 at their corresponding sites. These phosphorylated Smads dimerize with the coactivating Smad4 and translocate to the nucleus, where they stimulate transcription of target genes.

Primary endothelial cells (HUVEC: Human Umbilical Vein Endothelial Cells; supplier Promocell) are cultivated in the culture medium obtained from Promocell (with supplements corresponding to 5% FCS) for maximum 5 passages, seeded into black 384-well culture plates with clear bottom (3000 cells/well/30 μl), and incubated for 16-24 hours at 37° C., 5% CO2 and 90% rH.

The following day cells were serum-starved for 2-3 h in order to stop TGF-ß-mediated signalling derived from ligands present in FBS. 1.5 ng/ml BMP-9 was than added in parallel with test compounds for 2 h at 37° C., 5% CO2 in order to identify compounds which block functional activity of ALK1 leading to phosphorylation and nuclear translocation of SMAD1/5/8.

After fixation (15 min 4% Formaldehyd in PBS) and permeabilization (10 min 0.2% Triton X-100 in PBS) an indirect immunocytochemical staining is performed with a specific Phospho-Smad1/5 (Ser463/465) antibody (Cell Signaling #9516) and Alexa488-labelled secondary anti-rabbit-IgG-antibody. DNA staining with Propidium Iodide allowed parallel cell counting. Image acquisition and analysis was performed on an MDS ImageXpress Ultra confocal High Content Reader using the image analysis software MetaXpress. Final read-out were % nuclei with a pSMAD1/5 signal above a defined background.

The final DMSO concentration in the assay was 0.5%. DMSO-treated HUVEC cells served as neutral control (=0%) and cells treated with 10 μM of a reference inhibitor described in a patent served as inhibitor control (=−100%). Raw data were normalised to the neutral and inhibitory references. The assay was performed as dose response (10 compound dilutions, 1 nM-30 μM).

Pharmacological Data

TABLE 1

Inhibition (IC$_{50}$) of ALK1, ALK2, ALK5 (TGFβR1) and Smad 1/5 of some representative compounds of the formula I

| Compound No. | ALK1 IC$_{50}$ [M] | ALK2 IC$_{50}$ [M] | ALK5 IC$_{50}$ [M] | Smad 1/5 IC$_{50}$ [M] |
|---|---|---|---|---|
| "A1" | 3.9E-8 | 9.4E-8 | 3.6E-6 | 1.3E-6 |
| "A2" | 1.4E-6 | 6.3E-7 | | |
| "A3" | 8.9E-6 | | | |
| "A4" | 9.2E-6 | 5.4E-6 | | |
| "A5" | 1E-05 | 5.7E-6 | | |
| "A6" | | | | |
| "A7" | | | | |
| "A8" | | | | |
| "A9" | | | | 5.7E-6 |

TABLE 1-continued

Inhibition (IC$_{50}$) of ALK1, ALK2, ALK5 (TGFβR1) and Smad 1/5 of some representative compounds of the formula I

| Compound No. | ALK1 IC$_{50}$ [M] | ALK2 IC$_{50}$ [M] | ALK5 IC$_{50}$ [M] | Smad 1/5 IC$_{50}$ [M] |
|---|---|---|---|---|
| "A10" | 9.5E-7 | 4.3E-7 | | |
| "A11" | | | | 6.5E-6 |
| "A12" | 2.8E-8 | 5.7E-8 | 4.1E-6 | 7.2E-6 |
| "A13" | 1E-9 | 1E-9 | 9.7E-7 | 4E-7 |
| "A14" | | | | 5.7E-6 |
| "A15" | 3.5E-6 | | | |
| "A16" | 6E-9 | 8E-9 | 2.4E-6 | 5.9E-7 |
| "A17" | 2.7E-8 | 2.5E-8 | 3.3E-6 | 2.5E-6 |
| "A18" | | | | 2E-6 |
| "A19" | | | | 1.1E-5 |
| "A20" | 2.4E-8 | 1.9E-8 | 4.4E-6 | 7.8E-6 |
| "A21" | 8.6E-9 | 2.3E-8 | 5.1E-6 | 6.1E-6 |
| "A22" | 3.5E-9 | 1.6E-8 | 2.1E-6 | 3.3E-6 |
| "A23" | 2E-9 | 2.2E-8 | 1.6E-6 | 1.3E-7 |
| "A24" | 3.3E-8 | 4.1E-8 | 6.5E-6 | |
| "A25" | 3.2E-9 | 2.1E-8 | 2.6E-6 | 2.7E-6 |
| "A26" | 5E-9 | 3.1E-8 | 1.9E-6 | 1.8E-6 |
| "A27" | 1.3E-8 | 1.2E-8 | 1.7E-6 | 4.5E-7 |
| "A28" | | 9.9E-8 | | |
| "A29" | 9.2E-8 | 6.3E-8 | 1.7E-6 | 3.7E-6 |
| "A30" | 1.8E-6 | 7.1E-7 | | |
| "A31" | 5.5E-6 | 3.4E-6 | | |
| "A32" | | | | |
| "A33" | 1.4E-8 | 1.1E-8 | 1.9E-6 | 9E-7 |
| "A34" | 3.0E-8 | 2.0E-8 | 4.8E-6 | 2E-6 |
| "A35" | 1.6E-8 | 1.1E-8 | 3.2E-6 | 7.2E-7 |
| "A36" | 2.9E-8 | 2.2E-8 | 1.1E-6 | 2.4E-7 |
| "A37" | 4E-9 | 3E-8 | 2.5E-6 | |
| "A38" | 3.7E-9 | 1.9E-8 | 3.2E-7 | |
| "A39" | 1.9E-7 | 1.2E-7 | | |
| "A40" | 7.3E-8 | 5.6E-8 | 8.1E-6 | 5.2E-6 |
| "A41" | 1E-8 | 7E-9 | 4.3E-7 | 1.9E-7 |
| "A42" | | | | 7.9E-6 |
| "A43" | 4.5E-8 | 3.7E-8 | 8.7E-7 | 1.8E-6 |
| "A44" | 4E-9 | 6E-9 | 1.4E-7 | 1E-5 |
| "A45" | | | | 5E-6 |
| "A46" | | | | 4.4E-6 |
| "A47" | 1E-9 | 3.8E-8 | 2.0E-7 | |
| "A48" | 1.7E-8 | 2.2E-8 | 1.4E-6 | 1E-6 |
| "A48a" | 4.9E-8 | 4.4E-8 | 1.3E-7 | 2.7E-6 |
| "A49" | 1.4E-9 | 2.6E-8 | 2.8e-7 | 3.7E-6 |
| "A50" | 2E-9 | 5E-9 | 1.7E-7 | 4E-7 |
| "A51" | 1.2E-7 | 1.0E-7 | 1E-5 | 5.6E-6 |
| "A52" | 2.9E-8 | 1.7E-8 | 4.8E-7 | 2.6E-6 |
| "A53" | | | | 2.8E-6 |
| "A54" | 2.6E-6 | 1.1E-6 | | |
| "A55" | 6.8E-6 | 3.1E-6 | | |
| "A56" | | | | |
| "A57" | 3.1E-6 | | | |
| "A58" | 3.3E-6 | 3.1E-6 | | |
| "A59" | 1.7E-7 | 8.0E-8 | 2.5E-6 | 1.2E-5 |
| "A60" | | | | |

Explanation: 1.4 E-6 means $1.4 \times 10^{-6}$

The compounds shown in Table 1 are particularly preferred compounds according to the invention.

Synthesis of Intermediates o-Phenylenediamine Derivatives:

Synthesis of tert-butyl 4-(3,4-diaminophenyl)piperazine-1-carboxylate

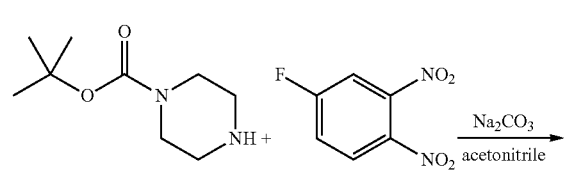

-continued

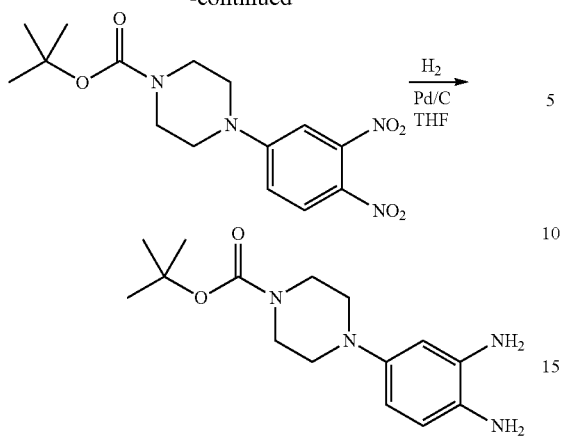

To a solution of tert-butyl piperazine-1-carboxylate (5.74 g, 30.8 mmol) and 4-fluoro-1,2-dinitro-benzene (5.74 g, 30.8 mmol) in acetonitrile (60 ml) is added sodium carbonate (3.27 g, 30.8 mmol) and the resulting suspension is stirred for 20 hours at room temperature. The reaction mixture is diluted with water and acetonitrile is evaporated in vacuo. The solid is filtered off and dried under vacuum. The residue is triturated with tert-butyl methyl ether to afford tert-butyl 4-(3,4-dinitrophenyl)piperazine-1-carboxylate as yellow crystals; HPLC/MS 1.59 min, [M-isobutene]$^+$297, $^1$H NMR (400 MHz, DMSO-d6) δ 8.10 (d, J=9.5 Hz, 1H), 7.47 (d, J=2.8 Hz, 1H), 7.13 (dd, J=9.6, 2.8 Hz, 1H), 3.62-3.53 (m, 4H), 3.53-3.40 (m, 4H), 1.42 (s, 9H).

To a suspension of tert-butyl 4-(3,4-dinitrophenyl)piperazine-1-carboxylate (9.03 g, 25.6 mmol) in THF (90 ml) is added moist palladium on charcoal (5% Pd, approx. 54% water, 2.2 g) and the mixture is hydrogenated for 22 hours at room temperature and atmospheric pressure. The catalyst is filtered off and the filtrate is evaporated in vacuo. The residue is triturated with tert-butyl methyl ether to afford tert-butyl 4-(3,4-diaminophenyl)piperazine-1-carboxylate as light gray powder; HPLC/MS 1.06 min, [M+H]$^+$293;

$^1$H NMR (400 MHz, DMSO-d6) δ 6.40 (d, J=8.3 Hz, 1H), 6.23 (d, J=2.7 Hz, 1H), 6.03 (dd, J=8.3, 2.6 Hz, 1H), 4.36 (s, 2H), 4.02 (s, 2H), 3.40 (t, J=5.1 Hz, 4H), 2.85-2.72 (m, 4H), 1.41 (s, 9H).

The following compounds are prepared similarly:

5-Morpholin-4-yl-2-nitro-phenylamine

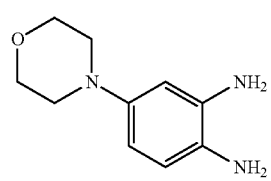

dark brown solid; HPLC/MS 0.72 min, [M+H]$^+$194;

$^1$H NMR (400 MHz, DMSO-d$_6$) δ 6.40 (d, J=8.3 Hz, 1H), 6.20 (d, J=2.6 Hz, 1H), 6.02-5.99 (m, 1H), 4.36 (br s, 2H), 3.98 (br s, 2H), 3.67 (t, J=4.6 Hz, 4H), 2.83 (t, J=4.8 Hz, 4H).

5-Morpholin-4-yl-2-nitro-phenylamine

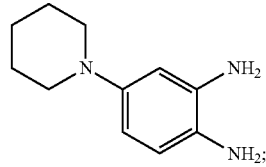 [SMILES: Nc1ccc(N2CCCCC2)cc1N]

dark brown oil; HPLC/MS 0.95 min, [M+H]$^+$193.

tert-Butyl 3-(3,4-diaminophenyl)-3,8-diazabicyclo[3.2.1]octane-8-carboxylate

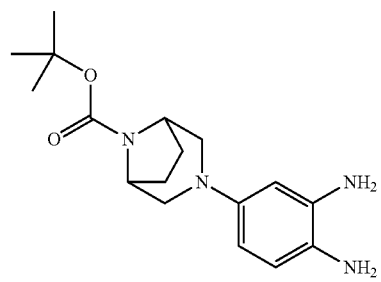 [SMILES: CC(C)(C)OC(=O)N1C2CCC1CN(c1ccc(N)c(N)c1)C2]

light gray solid; HPLC/MS 1.13 min, [M+H]$^+$319;

$^1$H NMR (400 MHz, DMSO-d$_6$) δ 6.40 (d, J=8.3 Hz, 1H), 6.16 (d, J=2.7 Hz, 1H), 5.97 (dd, J=8.4, 2.7 Hz, 1H), 4.35 (s, 2H), 4.16 (s, 2H), 3.94 (s, 2H), 3.32 (s, 2H), 3.17 (d, J=10.3 Hz, 2H), 2.72-2.58 (m, 2H), 1.92-1.69 (m, 4H), 1.42 (s, 9H).

tert-Butyl 4-(3,4-diaminophenyl)-1,4-diazepane-1-carboxylate

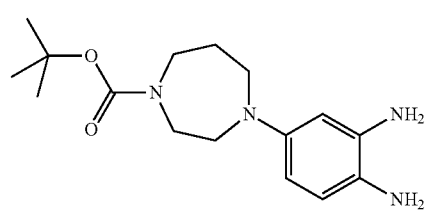 [SMILES: CC(C)(C)OC(=O)N1CCCN(c2ccc(N)c(N)c2)CC1]

dark brown foam; HPLC/MS 1.09 min, [M+H]$^+$307.

1-(3,4-Diamino-phenyl)-piperidin-4-ol

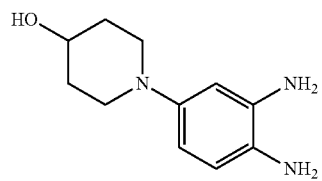 [SMILES: Nc1ccc(N2CCC(O)CC2)cc1N]

dark brown solid; HPLC/MS 0.27 min, [M+H]$^+$208.

[1-(3,4-Diamino-phenyl)-piperidin-4-yl]-carbamic acid tert-butyl ester

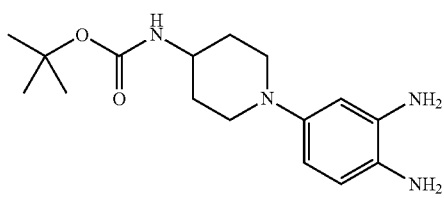 [SMILES: CC(C)(C)OC(=O)NC1CCN(c2ccc(N)c(N)c2)CC1]

brown solid; HPLC/MS 0.96 min, [M+H]$^+$307;
$^1$H NMR (400 MHz, DMSO-d$_6$) δ 6.77 (d, J=7.8 Hz, 1H), 6.39 (d, J=8.2 Hz, 1H), 6.23 (d, J=2.6 Hz, 1H), 6.03 (dd, J=8.3, 2.6 Hz, 1H), 4.32 (s, 2H), 3.94 (s, 2H), 3.3 (m, 5H), 1.76 (d, J=12.2 Hz, 2H), 1.49 (m, 2H), 1.40 (s, 9H).

2-(5-Bromo-2-methoxy-3-pyridyl)-1H-benzimidazole derivatives

Synthesis of tert-butyl 4-[2-(5-bromo-2-methoxy-3-pyridyl)-1H-benzimidazol-5-yl]piperazine-1-carboxylate

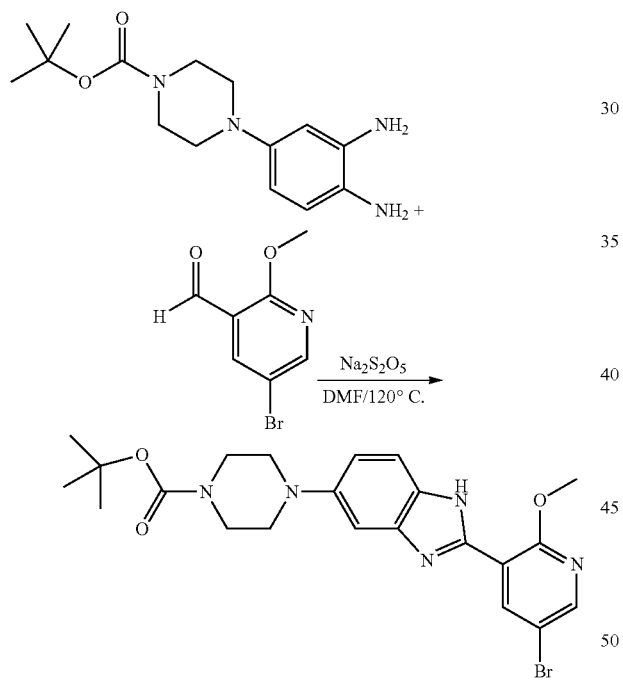

To a solution of 5-bromo-2-methoxy-pyridine-3-carbaldehyde (2.16 g, 10.0 mmol) and tert-butyl 4-(3,4-dinitrophenyl)piperazine-1-carboxylate (2.92 g, 10.0 mmol) in DMF (20 ml) is added sodium disulfite (5.70 g, 30 mmol). The resultant suspension is heated to 120° C. and stirred at this temperature for 30 minutes. The reaction mixture is allowed to cool to room temperature and poured into water (800 ml). The resultant precipitate is filtered off, washed with water and dried under vacuum. The residue is triturated with tert-butyl methyl ether to afford tert-butyl 4-[2-(5-bromo-2-methoxy-3-pyridyl)-1H-benzimidazol-5-yl]piperazine-1-carboxylate as light gray crystals; HPLC/MS 1.47 min, [M+H]$^+$488,490;
$^1$H NMR (500 MHz, DMSO-d$_6$, TFA-d$_1$) δ 8.80 (d, J=2.4 Hz, 1H), 8.64 (d, J=2.4 Hz, 1H), 7.80 (d, J=9.1 Hz, 1H), 7.47 (dd, J=9.2, 2.3 Hz, 1H), 7.33 (d, J=2.2 Hz, 1H), 4.19 (s, 3H), 3.62 (t, J=5.2 Hz, 4H), 3.33 (t, J=5.2 Hz, 4H), 1.46 (s, 9H).

The following compounds are prepared analogously 2-(5-Bromo-2-methoxy-pyridin-3-yl)-5-methoxy-1H-benzimidazole

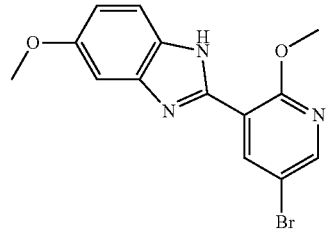

brown resin; HPLC/MS 2.365 min, [M+H]$^+$334,335.

2-(5-Bromo-2-methoxy-pyridin-3-yl)-5-piperidin-1-yl-1H-benzimidazole

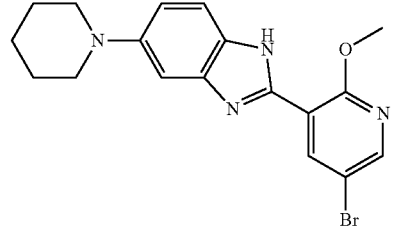 [SMILES: COc1ncc(Br)cc1-c1nc2cc(N3CCCCC3)ccc2[nH]1]

orange-brown solid; HPLC/MS 2.05 min, [M+H]$^+$387, 389.

3-[2-(5-Bromo-2-methoxy-pyridin-3-yl)-3H-benzimidazol-5-yl]-3,8-diaza-bicyclo[3.2.1]octane-8-carboxylic acid tert-butyl ester

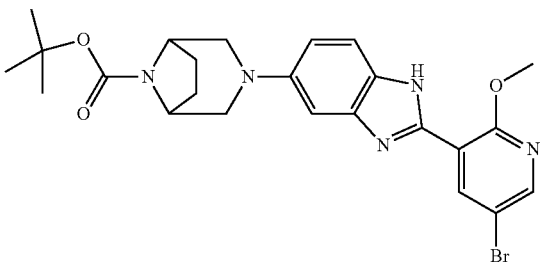 [SMILES: COc1ncc(Br)cc1-c1nc2cc(N3CC4CCC(C3)N4C(=O)OC(C)(C)C)ccc2[nH]1]

pale brown solid; HPLC/MS 1.52 min, [M+H]$^+$514,516.

4-[2-(5-Bromo-2-methoxy-pyridin-3-yl)-1H-benzoimidazol-5-yl]-[1,4]diazepane-1-carboxylic acid tert-butyl ester

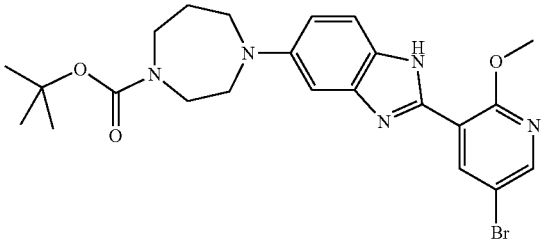 [SMILES: COc1ncc(Br)cc1-c1nc2cc(N3CCCN(C(=O)OC(C)(C)C)CC3)ccc2[nH]1]

beige solid; HPLC/MS 1.36 min, [M+H]$^+$502,504.

2-(5-Bromo-2-methoxy-pyridin-3-yl)-5-morpholin-4-yl-1H-benzimidazole

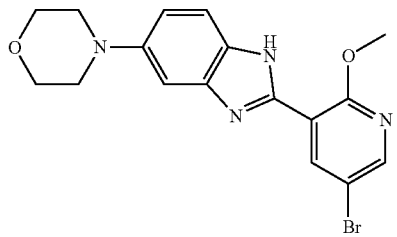 [SMILES: COc1ncc(Br)cc1-c1nc2cc(N3CCOCC3)ccc2[nH]1]

dark brown solid; HPLC/MS 2.19 min, [M+H]⁺389,391.

1-[2-(5-Bromo-2-methoxy-pyridin-3-yl)-1H-benzo-imidazol-5-yl]-piperidin-4-ol

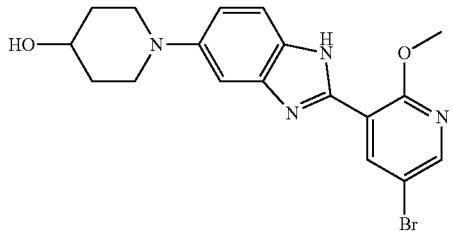 [SMILES: COc1ncc(Br)cc1-c1nc2cc(N3CCC(O)CC3)ccc2[nH]1]

brown gum; HPLC/MS 1.10 min, [M+H]⁺403,405;

$^1$H NMR (400 MHz, DMSO-d6, d-TFA) δ 8.78 (d, J=2.4 Hz, 1H), 8.60 (d, J=2.4 Hz, 1H), 8.10 (d, J=2.1 Hz, 1H), 7.99 (d, J=8.9 Hz, 1H), 7.83 (dd, J=9.0, 2.2 Hz, 1H), 4.14 (s, 3H), 3.96 (tt, J=7.5, 3.5 Hz, 1H), 3.78 (m, 2H), 3.60 (m, 2H), 2.13 (m, 2H), 1.95-1.83 (m, 2H).

{1-[2-(5-Bromo-2-methoxy-pyridin-3-yl)-1H-benzo-imidazol-5-yl]-piperidin-4-yl}-carbamic acid tert-butyl ester

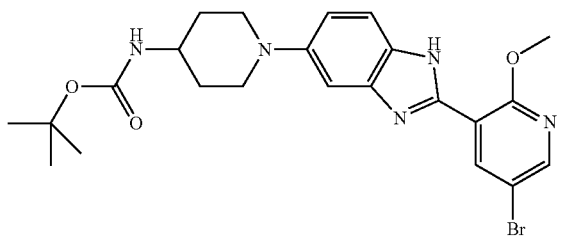 [SMILES: COc1ncc(Br)cc1-c1nc2cc(N3CCC(NC(=O)OC(C)(C)C)CC3)ccc2[nH]1]

yellow solid; HPLC/MS 1.29 min, [M+H]⁺502,504;

$^1$H NMR (400 MHz, DMSO-d$_6$, TFA-d$_1$) δ 8.77 (d, J=2.4 Hz, 1H), 8.59 (d, J=2.4 Hz, 1H), 8.08 (d, J=2.1 Hz, 1H), 7.98 (d, J=8.9 Hz, 1H), 7.84 (dd, J=9.1, 2.2 Hz, 1H), 4.13 (s, 3H), 3.80 (s, 1H), 3.77-3.62 (m, 4H), 2.11 (m, 2H), 1.90 (m, 2H), 1.39 (s, 9H).

EXAMPLES

5-(3-Hydroxymethyl-phenyl)-3-(5-morpholin-4-yl-1H-benzimidazol-2-yl)-1H-pyridin-2-one ("A1")

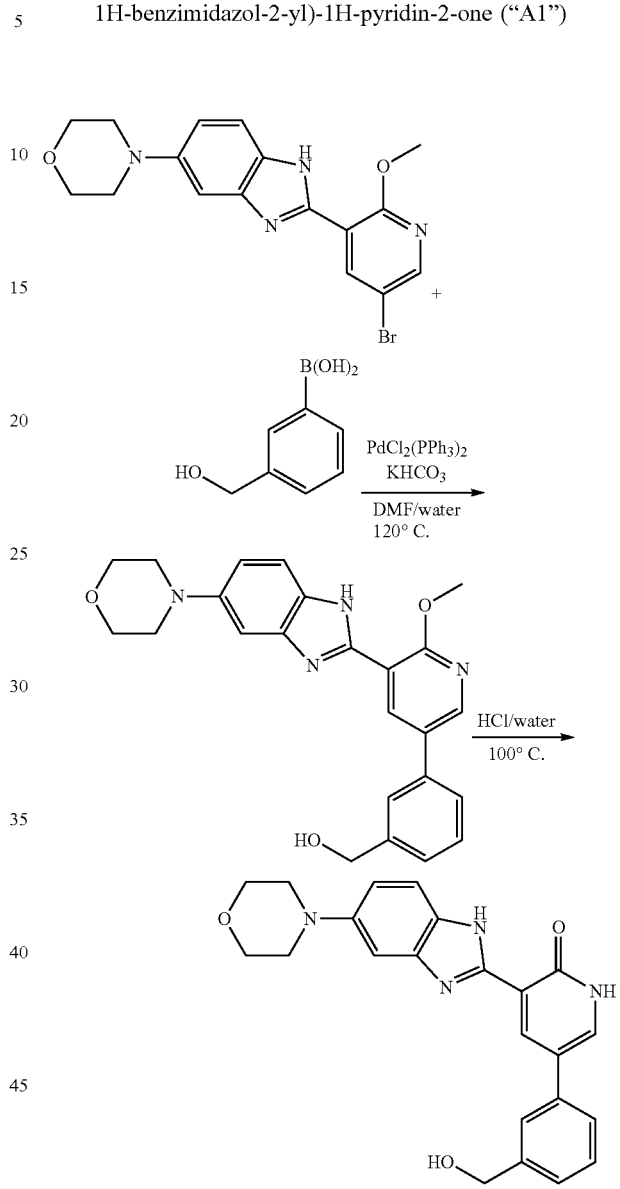

A microwave vial is charged with 2-(5-bromo-2-methoxy-pyridin-3-yl)-5-morpholin-4-yl-1H-benzimidazole (195 mg, 0.50 mmol), [3-(hydroxymethyl)-phenyl]boronic acid (85 mg, 0.56 mmol), potassium hydrogen carbonate (80 mg, 0.80 mmol), DMF (1.50 ml) and water (0.75 ml). The vial is flushed with nitrogen Then, bis(triphenylphosphine) palladium(II) chloride (8.0 mg, 11 µmol) is added under nitrogen and the reaction mixture is irradiated in a microwave reactor for 1 hour at 120° C. The reaction mixture is filtered over kieselguhr and the filter cake is washed with dichloromethane. The filtrate is evaporated and the residue is chromatographed on a silica gel column with dichloromethane/methanol as eluent to afford {3-[6-methoxy-5-(5-morpholin-4-yl-1H-benzimidazol-2-yl)-pyridin-3-yl]-phenyl}-methanol as brown solid; HPLC/MS 1.16 min, [M+H]⁺ 417.

A microwave vial is charged with {3-[6-methoxy-5-(5-morpholin-4-yl-1H-benzimidazol-2-yl)-pyridin-3-yl]-phenyl}-methanol (83.3 mg, 0.20 mmol), water (1 ml) and aqueous hydrochloric acid (37% by weight, 1 ml). The vial is irradiated in the microwave reactor for 15 minutes at 100° C. The reaction mixture is absorbed on kieselguhr and chromatographed on a silica gel column with dichloromethane/methanol as eluent to afford 5-(3-hydroxymethyl-phenyl)-3-(5-morpholin-4-yl-1H-benzimidazol-2-yl)-1H-pyridin-2-one as yellow crystals; HPLC/MS 1.06 min, [M+H]$^+$ 403;

$^1$H NMR (500 MHz, DMSO-d$_6$, TFA-d$_1$) δ 9.03 (d, J=2.7 Hz, 1H), 8.24 (d, J=2.7 Hz, 1H), 7.81 (d, J=9.6 Hz, 1H), 7.68 (s, 1H), 7.58 (d, J=8.2 Hz, 1H), 7.45 (d, J=7.6 Hz, 1H), 7.43-7.39 (m, 3H), 7.34 (d, J=7.6 Hz, 1H), 4.60 (s, 2H), 3.86-3.76 (m, 4H), 3.30 (t, J=4.9 Hz, 4H).

The following compounds are prepared analogously:

3-(1H-Benzimidazol-2-yl)-5-quinolin-4-yl-1H-pyridin-2-one ("A2")

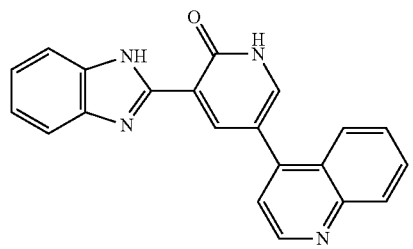 [SMILES: O=c1[nH]cc(-c2ccnc3ccccc23)cc1-c1nc2ccccc2[nH]1]

light brown crystals, MS-ESI: [M+H]$^+$339; $^1$H NMR (400 MHz, DMSO-d$_6$) δ 12.93 (s, 1H), 12.63 (s, 1H), 8.97 (d, J=4.4 Hz, 1H), 8.75 (d, J=2.7 Hz, 1H), 8.14 (d, J=8.5 Hz, 1H), 8.05 (d, J=7.5 Hz, 1H), 7.96 (d, J=2.6 Hz, 1H), 7.84 (ddd, J=8.4, 6.8, 1.4 Hz, 1H), 7.80-7.48 (m, 4H), 7.18 (m, 2H).

5-(5-Chloro-1H-benzimidazol-2-yl)-1H-[3,4']bipyridinyl-6-one ("A3")

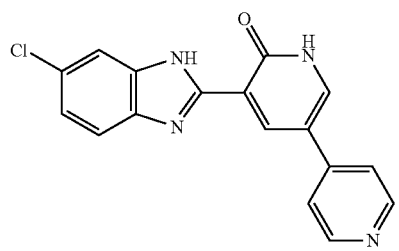 [SMILES: O=c1[nH]cc(-c2ccncc2)cc1-c1nc2ccc(Cl)cc2[nH]1]

grey crystals, MS-ESI: [M+H]$^+$323; $^1$H NMR (400 MHz, DMSO-d$_6$, TFA-d$_1$) δ 9.38 (d, J=2.8 Hz, 1H), 9.06 (d, J=6.1 Hz, 2H), 9.02 (d, J=2.8 Hz, 1H), 8.49 (d, J=6.2 Hz, 2H), 8.07 (d, J=1.9 Hz, 1H), 8.01 (d, J=8.8 Hz, 1H), 7.64 (dd, J=8.8, 2.1 Hz, 1H).

5-(5-Methyl-1H-benzimidazol-2-yl)-1H-[3,4']bipyridinyl-6-one ("A4")

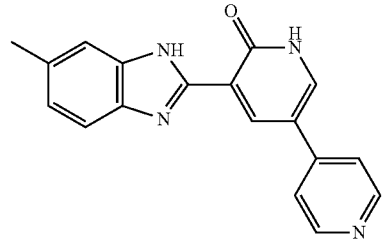 [SMILES: Cc1ccc2nc(-c3cc(-c4ccncc4)c[nH]c3=O)[nH]c2c1]

light green crystals, MS-ESI: [M+H]$^+$303; $^1$H NMR (500 MHz, DMSO-d$_6$, TFA-d$_1$) δ 9.29 (d, J=2.7 Hz, 1H), 9.02 (d, J=6.2 Hz, 2H), 8.94 (d, J=2.7 Hz, 1H), 8.44 (d, J=6.2 Hz, 2H), 7.83 (d, J=8.4 Hz, 1H), 7.72 (s, 1H), 7.41 (d, J=8.5 Hz, 1H), 2.51 (s, 3H).

5-(4-Methyl-1H-benzimidazol-2-yl)-1H-[3,4']bipyridinyl-6-one ("A5")

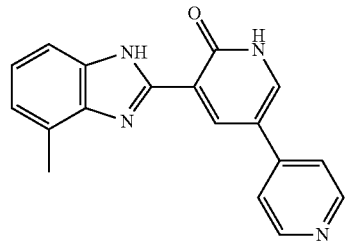 [SMILES: Cc1cccc2[nH]c(-c3cc(-c4ccncc4)c[nH]c3=O)nc12]

light brown crystals, MS-ESI: [M+H]$^+$303; $^1$H NMR (500 MHz, DMSO-d$_6$, TFA-d$_1$) δ 9.35 (d, J=2.8 Hz, 1H), 9.00 (d, J=6.7 Hz, 2H), 8.92 (d, J=2.8 Hz, 1H), 8.44 (d, J=6.6 Hz, 2H), 7.79 (d, J=8.2 Hz, 1H), 7.43 (t, J=7.8 Hz, 1H), 7.36 (d, J=7.4 Hz, 1H), 2.68 (s, 3H).

5-(5,6-Dimethoxy-1H-benzimidazol-2-yl)-1H-[3,4']bipyridinyl-6-one ("A6")

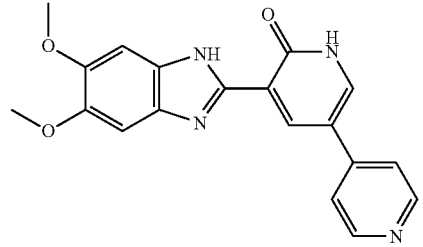 [SMILES: COc1cc2nc(-c3cc(-c4ccncc4)c[nH]c3=O)[nH]c2cc1OC]

yellow solid, MS-ESI: [M+H]$^+$349; $^1$H NMR (500 MHz, DMSO-d$_6$, TFA-d$_1$) δ 9.29 (d, J=2.4 Hz, 1H), 9.05 (d, J=6.6 Hz, 2H), 8.92 (d, J=2.8 Hz, 1H), 8.48 (d, J=6.7 Hz, 2H), 7.43 (s, 2H), 3.93 (s, 6H).

2-(6-Oxo-1,6-dihydro-[3,4']bipyridinyl-5-yl)-1H-benzimidazole-5-carbonitrile ("A7")

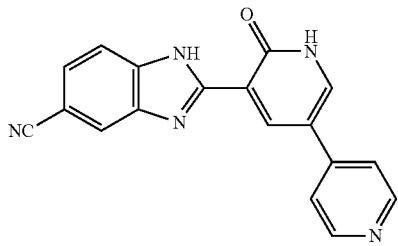 [SMILES: N#Cc1ccc2[nH]c(-c3cc(-c4ccncc4)c[nH]c3=O)nc2c1]

MS-ESI: [M+H]$^+$314; $^1$H NMR (400 MHz, DMSO-d$_6$, TFA-d$_1$) δ 9.36 (d, J=2.8 Hz, 1H), 9.01 (d, J=7.0 Hz, 2H), 8.98 (d, J=2.7 Hz, 1H), 8.45 (d, J=7.1 Hz, 2H), 8.43-8.42 (m, 2H), 8.09 (d, J=8.5 Hz, 1H), 7.90 (dd, J=8.5, 1.5 Hz, 1H).

Methyl 2-[2-oxo-5-(4-pyridyl)-1H-pyridin-3-yl]-1H-benzimidazole-5-carboxylate ("A8")

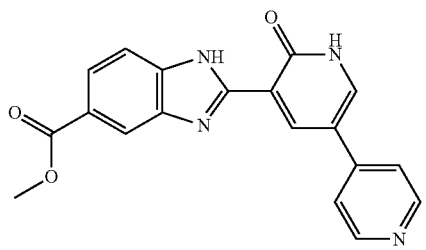 [SMILES: COC(=O)c1ccc2[nH]c(-c3cc(-c4ccncc4)c[nH]c3=O)nc2c1]

MS-ESI: [M+H]$^+$347; $^1$H NMR (500 MHz, DMSO-d$_6$, TFA-d$_1$) δ 9.43 (d, J=2.7 Hz, 1H), 9.06 (d, J=6.4 Hz, 2H), 9.02 (d, J=2.8 Hz, 1H), 8.57 (d, J=1.6 Hz, 1H), 8.51 (d, J=6.5 Hz, 2H), 8.19 (dd, J=8.6, 1.5 Hz, 1H), 8.08 (d, J=8.6 Hz, 1H), 3.96 (s, 3H).

3-(6-Morpholin-4-yl-1H-benzimidazol-2-yl)-5-quinolin-4-yl-1H-pyridin-2-one ("A9")

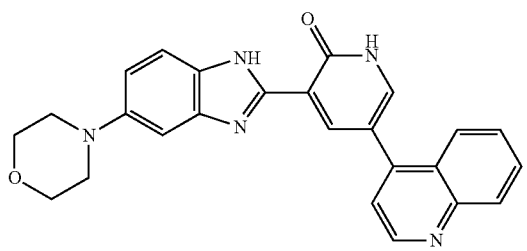 [SMILES: O=c1[nH]cc(-c2ccnc3ccccc23)cc1-c1nc2cc(N3CCOCC3)ccc2[nH]1]

MS-ESI: [M+H]$^+$424; $^1$H NMR (400 MHz, DMSO-d$_6$, TFA-d$_1$) δ 9.51 (d, J=5.7 Hz, 1H), 9.05 (d, J=2.6 Hz, 1H), 8.53-8.42 (m, 3H), 8.26 (m, 2H), 8.05 (dd, J=8.5, 7.0 Hz, 1H), 7.88 (d, J=9.0 Hz, 1H), 7.53-7.43 (m, 2H), 3.89 (dd, J=6.1, 3.5 Hz, 4H), 3.44-3.31 (m, 4H).

3-[5-(Pyridin-4-yloxy)-1H-benzimidazol-2-yl]-5-quinolin-4-yl-1H-pyridin-2-one ("A10")

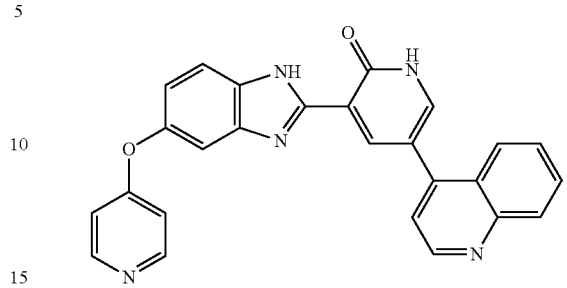

MS-ESI: [M+H]$^+$432; $^1$H NMR (500 MHz, DMSO-d$_6$, TFA-d$_1$) δ 9.48 (d, J=5.6 Hz, 1H), 9.08 (d, J=2.6 Hz, 1H), 8.88 (d, J=7.4 Hz, 2H), 8.54 (d, J=2.6 Hz, 1H), 8.46 (d, J=8.7 Hz, 1H), 8.42 (d, J=8.5 Hz, 1H), 8.31-8.21 (m, 2H), 8.13 (d, J=8.9 Hz, 1H), 8.03 (ddd, J=8.3, 7.0, 1.2 Hz, 1H), 7.94 (d, J=2.2 Hz, 1H), 7.62-7.50 (m, 3H).

5-(2-Chloro-5-hydroxymethyl-phenyl)-3-(5-morpholin-4-yl-1H-benzimidazol-2-yl)-1H-pyridin-2-one ("A11")

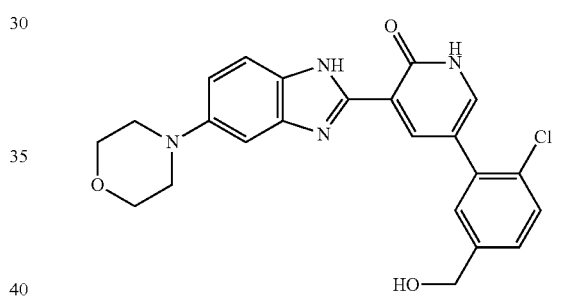

HPLC/MS 1.09 min, [M+H]$^+$437; $^1$H NMR (400 MHz, DMSO-d$_6$, TFA-d$_1$) δ 8.77 (d, J=2.6 Hz, 1H), 8.05 (d, J=2.6 Hz, 1H), 7.79 (d, J=9.8 Hz, 1H), 7.52 (d, J=8.2 Hz, 1H), 7.48 (d, J=1.6 Hz, 1H), 7.44-7.33 (m, 3H), 4.56 (s, 2H), 3.83 (t, J=5.0 Hz, 4H), 3.30 (t, J=4.9 Hz, 4H).

5-(3-Hydroxymethyl-phenyl)-3-[5-(4-hydroxy-piperidin-1-yl)-1H-benzimidazol-2-yl]-1H-pyridin-2-one ("A12")

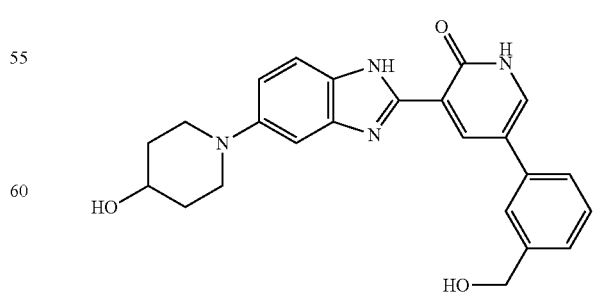

yellow solid; HPLC/MS 0.97 min, [M+H]$^+$417; $^1$H NMR (500 MHz, DMSO-d$_6$) δ 9.12 (d, J=2.7 Hz, 1H), 8.32 (d, J=2.7 Hz, 1H), 8.20 (d, J=2.2 Hz, 1H), 8.07 (d, J=9.0 Hz, 1H), 7.88 (dd, J=9.0, 2.2 Hz, 1H), 7.69 (s, 1H), 7.59 (dt, J=7.8, 1.4 Hz, 1H), 7.44 (t, J=7.7 Hz, 1H), 7.35 (d, J=7.6 Hz, 1H), 4.60 (s, 2H), 3.97 (tt, J=7.4, 3.5 Hz, 1H), 3.77 (ddd, J=11.4, 7.4, 3.7 Hz, 2H), 3.62 (ddd, J=11.6, 7.9, 3.6 Hz, 2H), 2.14 (m, 2H), 1.91 (m, 2H).

5-(3-Hydroxymethyl-phenyl)-3-(5-piperazin-1-yl-1H-benzimidazol-2-yl)-1H-pyridin-2-one dihydrochloride ("A13")

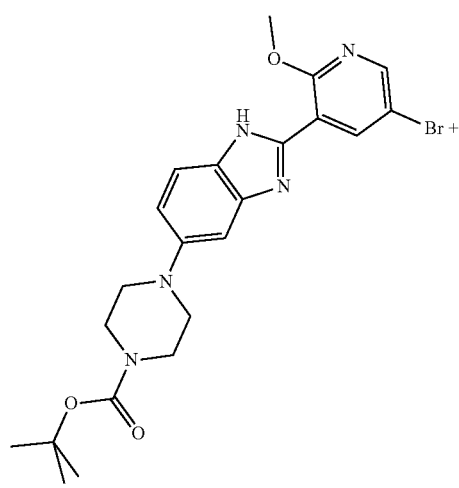

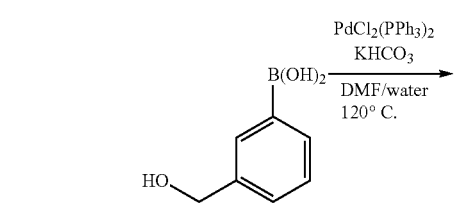

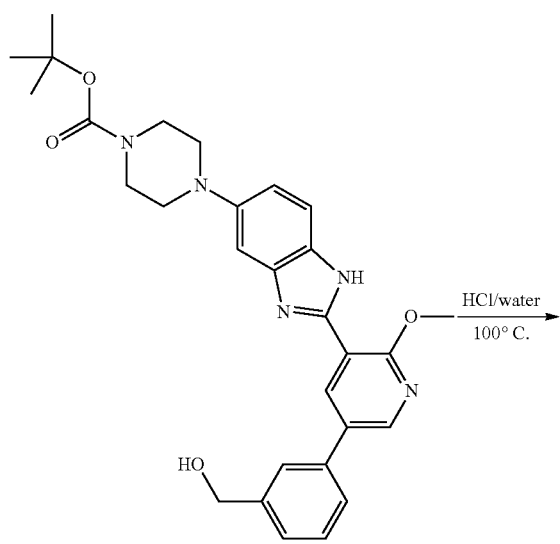

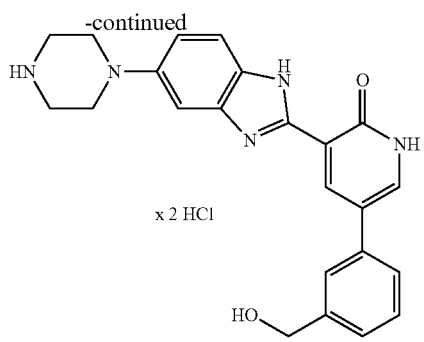

A microwave vial is charged with 4-[2-(5-bromo-2-methoxy-pyridin-3-yl)-1H-benzimidazol-5-yl]-piperazine-1-carboxylic acid tert-butyl ester (488 mg, 1.00 mmol), [3-(hydroxymethyl)phenyl]boronic acid (182 mg, 1.20 mmol), potassium hydrogen carbonate (101 mg, 1.20 mmol), DMF (4.0 ml) and water (1.0 ml). The vial is flushed with nitrogen Then, bis(triphenylphosphine)-palladium(II) chloride (14 mg, 20 μmol) is added under nitrogen and the reaction mixture is irradiated in a microwave reactor for 1 hour at 120° C. The reaction mixture is quenched with water. the resultant precipitate is filtered off, washed with water and dried under vacuum to afford 4-{2-[5-(3-hydroxymethyl-phenyl)-2-methoxy-pyridin-3-yl]-1H-benzimidazol-5-yl}-piperazine-1-carboxylic acid tert-butyl ester as yellow solid; HPLC/MS 1.31 min, [M+H]$^+$516; $^1$H NMR (500 MHz, DMSO-d$_6$, TFA-d$_1$) δ 8.93 (d, J=2.4 Hz, 1H), 8.85 (d, J=2.4 Hz, 1H), 7.84 (d, J=9.1 Hz, 1H), 7.81 (s, 1H), 7.70 (dt, J=7.9, 1.4 Hz, 1H), 7.53 (t, J=7.7 Hz, 1H), 7.50 (dd, J=9.2, 2.3 Hz, 1H), 7.45 (dt, J=7.8, 1.2 Hz, 1H), 7.41 (d, J=2.2 Hz, 1H), 4.68 (s, 2H), 4.27 (s, 3H), 3.64 (t, J=5.2 Hz, 4H), 3.36 (t, J=5.2 Hz, 4H), 1.47 (s, 9H).

To 4-{2-[5-(3-hydroxymethyl-phenyl)-2-methoxy-pyridin-3-yl]-1H-benzimidazol-5-yl}-piperazine-1-carboxylic acid tert-butyl ester (510 mg, 0.99 mmol) are added water (3.5 ml) and aqueous hydrochloric acid (37% by weight, 4.4 ml). The resulting suspension is stirred for 14 hours at 80° C. The reaction mixture is concentrated and reduced pressure and the residue is triturated with ethanol to afford 5-(3-hydroxymethyl-phenyl)-3-(5-piperazin-1-yl-1H-benzimidazol-2-yl)-1H-pyridin-2-one dihydrochloride as orange crystals; HPLC/MS 0.92 min, [M+H]$^+$402; $^1$H NMR (400 MHz, DMSO-d$_6$) δ 14.99 (bs, 1H), 14.85 (bs, 1H), 13.34 (s, 1H), 9.46 (s, 2H), 9.41 (d, J=2.6 Hz, 1H), 8.28 (s, 1H), 7.82-7.76 (m, 2H), 7.72 (dt, J=7.9, 1.3 Hz, 1H), 7.45 (t, J=7.7 Hz, 1H), 7.40-7.32 (m, 2H), 7.27 (d, J=2.3 Hz, 1H), 4.60 (s, 2H), 3.47 (m, 4H), 3.28 (m, 4H).

The following compounds are prepared analogously:

3-(6-Piperazin-1-yl-1H-benzimidazol-2-yl)-5-quinolin-4-yl-1H-pyridin-2-one ("A14")

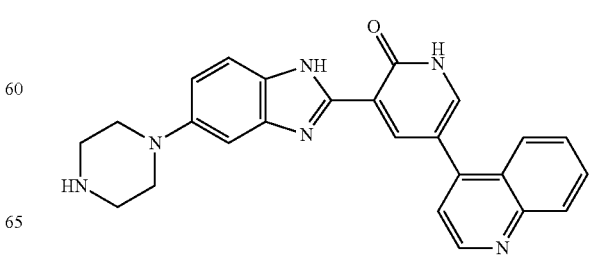

MS-ESI: [M+H]⁺423; ¹H NMR (500 MHz, DMSO-d₆, TFA-d₁) δ 9.51 (d, J=5.7 Hz, 1H), 9.04 (d, J=2.6 Hz, 1H), 8.50-8.44 (m, 3H), 8.31-8.22 (m, 2H), 8.04 (ddd, J=8.4, 6.9, 1.1 Hz, 1H), 7.84 (d, J=9.1 Hz, 1H), 7.39 (dd, J=9.1, 2.3 Hz, 1H), 7.35 (d, J=2.2 Hz, 1H), 3.49 (dd, J=6.9, 3.7 Hz, 4H), 3.37 (dd, J=6.7, 3.8 Hz, 4H).

5-(1H-Indol-3-yl)-3-(6-piperazin-1-yl-1H-benzimidazol-2-yl)-1H-pyridin-2-one ("A15")

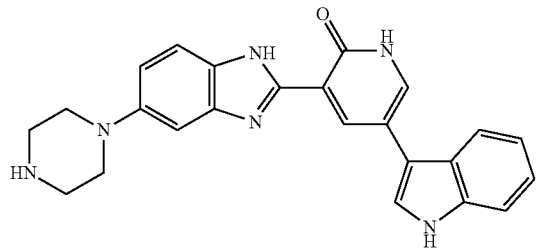 [SMILES: O=c1[nH]cc(-c2c[nH]c3ccccc23)cc1-c1nc2cc(N3CCNCC3)ccc2[nH]1]

MS-ESI: [M+H]⁺411; ¹H NMR (400 MHz, DMSO-d₆, TFA-d₁) δ 9.22 (d, J=2.6 Hz, 1H), 8.45 (d, J=2.6 Hz, 1H), 7.86 (d, J=8.9 Hz, 1H), 7.59 (d, J=7.8 Hz, 1H), 7.45-7.37 (m, 3H), 7.15 (t, J=7.5 Hz, 1H), 7.06 (t, J=7.5 Hz, 1H), 3.48 (dd, J=6.7, 3.6 Hz, 4H), 3.36 (dd, J=6.8, 3.6 Hz, 4H).

5-(4-Hydroxymethyl-phenyl)-3-(5-piperazin-1-yl-1H-benzimidazol-2-yl)-1H-pyridin-2-one ("A16")

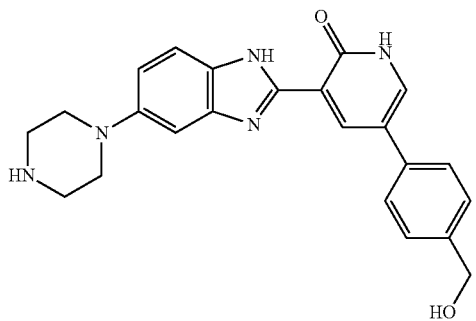 [SMILES: O=c1[nH]cc(-c2ccc(CO)cc2)cc1-c1nc2cc(N3CCNCC3)ccc2[nH]1]

HPLC/MS 0.91 min, [M+H]⁺402; ¹H NMR (400 MHz, DMSO-d₆, TFA-d₁) δ 9.05 (d, J=2.6 Hz, 1H), 8.10 (d, J=2.6 Hz, 1H), 7.71 (d, J=9.0 Hz, 1H), 7.60 (d, J=8.3 Hz, 2H), 7.40 (d, J=8.1 Hz, 2H), 7.28 (d, J=2.2 Hz, 1H), 7.23 (dd, J=9.1, 2.3 Hz, 1H), 4.52 (s, 2H), 3.41 (dd, J=7.0, 3.6 Hz, 4H), 3.34-3.23 (m, 4H).

3-(5-[1,4]Diazepan-1-yl-1H-benzimidazol-2-yl)-5-(3-hydroxymethyl-phenyl)-1H-pyridin-2-one ("A17")

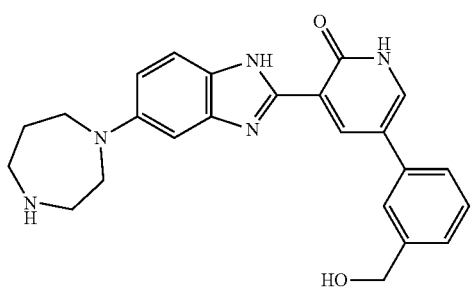 [SMILES: O=c1[nH]cc(-c2cccc(CO)c2)cc1-c1nc2cc(N3CCCNCC3)ccc2[nH]1]

orange solid, HPLC/MS 0.94 min, [M+H]⁺416; ¹H NMR (400 MHz, DMSO-d₆, TFA-d₁) δ 9.01 (d, J=2.7 Hz, 1H), 8.30-8.17 (m, 1H), 7.73 (d, J=9.1 Hz, 1H), 7.69 (s, 1H), 7.59 (d, J=8.1 Hz, 1H), 7.45 (t, J=7.7 Hz, 1H), 7.35 (d, J=7.6 Hz, 1H), 7.14 (d, J=9.3 Hz, 1H), 7.05 (d, J=2.4 Hz, 1H), 4.60 (s, 2H), 3.80 (t, J=5.1 Hz, 2H), 3.60 (t, J=6.1 Hz, 2H), 3.34 (t, J=5.1 Hz, 2H), 3.23-3.13 (m, 2H), 2.14 (p, J=6.2 Hz, 2H).

5-Furo[3,2-b]pyridin-7-yl-3-(5-piperazin-1-yl-1H-benzimidazol-2-yl)-1H-pyridin-2-one ("A18")

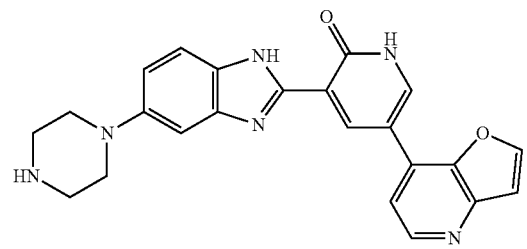 [SMILES: O=c1[nH]cc(-c2ccnc3ccoc23)cc1-c1nc2cc(N3CCNCC3)ccc2[nH]1]

orange solid, HPLC/MS 0.90 min, [M+H]⁺413; ¹H NMR (400 MHz, DMSO-d₆, TFA-d₁) δ 9.58 (d, J=2.7 Hz, 1H), 9.06 (d, J=6.3 Hz, 1H), 9.01 (d, J=2.6 Hz, 1H), 8.86 (d, J=2.3 Hz, 1H), 8.40 (d, J=6.4 Hz, 1H), 7.88 (d, J=9.7 Hz, 1H), 7.55 (d, J=2.3 Hz, 1H), 7.46-7.35 (m, 2H), 3.52 (m, 4H), 3.43-3.35 (m, 4H).

5-(3-Methoxymethyl-phenyl)-3-(5-piperazin-1-yl-1H-benzimidazol-2-yl)-1H-pyridin-2-one ("A19")

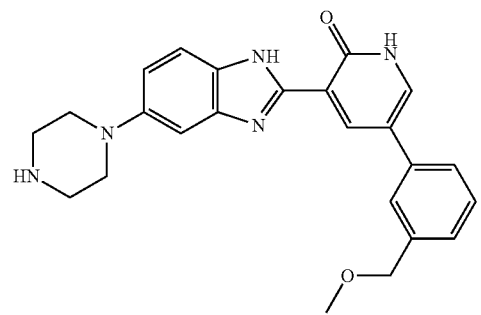 [SMILES: COCc1cccc(-c2c[nH]c(=O)c(-c3nc4cc(N5CCNCC5)ccc4[nH]3)c2)c1]

yellow solid, HPLC/MS 0.98 min, [M+H]⁺416; ¹H NMR (400 MHz, DMSO-d₆, TFA-d₁) δ 9.06 (d, J=2.7 Hz, 1H), 8.19 (d, J=2.7 Hz, 1H), 7.75 (d, J=8.9 Hz, 1H), 7.64 (s, 1H), 7.60 (d, J=7.9 Hz, 1H), 7.42 (t, J=7.7 Hz, 1H), 7.34-7.15 (m, 3H), 4.45 (s, 2H), 3.43 (m, 4H), 3.30 (m, 7H).

5-(4-Fluoro-3-hydroxymethyl-phenyl)-3-(5-piperazin-1-yl-1H-benzimidazol-2-yl)-1H-pyridin-2-one ("A20")

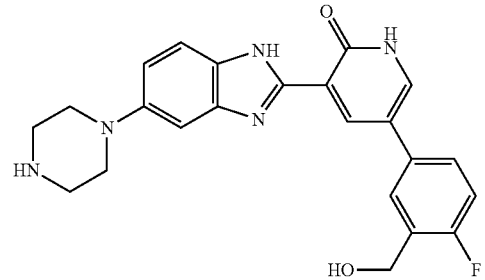 [SMILES: O=c1[nH]cc(-c2ccc(F)c(CO)c2)cc1-c1nc2cc(N3CCNCC3)ccc2[nH]1]

orange solid, HPLC/MS 0.95 min, [M+H]$^+$420; $^1$H NMR (400 MHz, DMSO-d$_6$, TFA-d$_1$) δ 9.13 (d, J=2.7 Hz, 1H), 8.27 (d, J=2.6 Hz, 1H), 7.88 (dd, J=6.9, 2.5 Hz, 1H), 7.83 (d, J=8.9 Hz, 1H), 7.69 (ddd, J=7.9, 4.8, 2.6 Hz, 1H), 7.43-7.34 (m, 2H), 7.28 (dd, J=9.8, 8.5 Hz, 1H), 4.69 (s, 2H), 3.50 (m, 5H), 3.37 (m, 4H).

5-(3,5-Difluoro-4-hydroxymethyl-phenyl)-3-(5-piperazin-1-yl-1H-benzimidazol-2-yl)-1H-pyridin-2-one dihydrochloride ("A21")

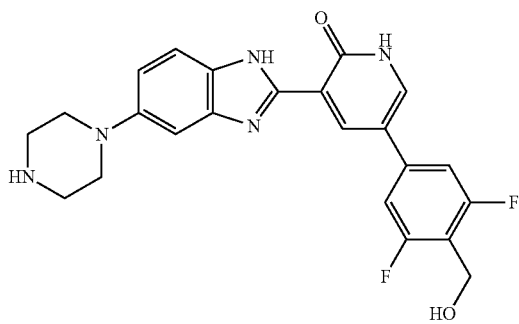 [SMILES: O=c1[nH]cc(-c2cc(F)c(CO)c(F)c2)cc1-c1nc2cc(N3CCNCC3)ccc2[nH]1]

yellow solid, HPLC/MS 0.91 min, [M+H]$^+$438; $^1$H NMR (500 MHz, DMSO-d$_6$, TFA-d$_1$) δ 9.25 (d, J=2.7 Hz, 1H), 8.49 (d, J=2.7 Hz, 1H), 7.83 (d, J=9.0 Hz, 1H), 7.61 (m, 2H), 7.39 (dd, J=9.1, 2.3 Hz, 1H), 7.35 (d, J=2.2 Hz, 1H), 4.57 (s, 2H), 3.49 m, 4H), 3.40-3.29 (m, 4H).

5-(2-Chloro-5-hydroxymethyl-phenyl)-3-(5-piperazin-1-yl-1H-benzimidazol-2-yl)-1H-pyridin-2-one dihydrochloride ("A22")

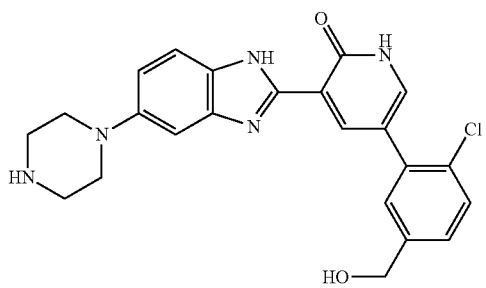 [SMILES: O=c1[nH]cc(-c2cc(CO)ccc2Cl)cc1-c1nc2cc(N3CCNCC3)ccc2[nH]1]

yellow solid, HPLC/MS 0.92 min, [M+H]$^+$436; $^1$H NMR (500 MHz, DMSO-d$_6$, TFA-d$_1$) δ 8.87 (d, J=2.6 Hz, 1H), 8.11 (d, J=2.6 Hz, 1H), 7.81 (d, J=9.0 Hz, 1H), 7.58 (d, J=8.2 Hz, 1H), 7.55 (d, J=2.1 Hz, 1H), 7.44 (dd, J=8.3, 2.1 Hz, 1H), 7.37 (dd, J=9.1, 2.3 Hz, 1H), 7.33 (d, J=2.2 Hz, 1H), 4.62 (s, 2H), 3.49 (m, 4H), 3.41-3.25 (m, 4H).

5-(2-Fluoro-3-hydroxymethyl-phenyl)-3-(5-piperazin-1-yl-1H-benzimidazol-2-yl)-1H-pyridin-2-one ("A23")

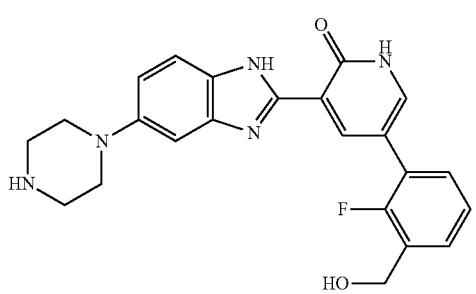 [SMILES: O=c1[nH]cc(-c2cccc(CO)c2F)cc1-c1nc2cc(N3CCNCC3)ccc2[nH]1]

orange powder, HPLC/MS 0.89 min, [M+H]$^+$420; $^1$H NMR (500 MHz, DMSO-d$_6$, TFA-d$_1$) δ 8.98 (d, J=2.6 Hz, 1H), 8.18 (d, J=2.5 Hz, 1H), 7.82 (d, J=9.1 Hz, 1H), 7.58 (m, 2H), 7.41-7.33 (m, 3H), 4.68 (s, 2H), 3.49 (m, 4H), 3.43-3.30 (m, 4H).

3-(5-[1,4]Diazepan-1-yl-1H-benzimidazol-2-yl)-5-(4-fluoro-3-hydroxymethyl-phenyl)-1H-pyridin-2-one ("A24")

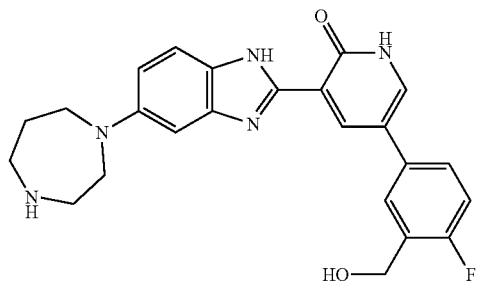 [SMILES: O=c1[nH]cc(-c2ccc(F)c(CO)c2)cc1-c1nc2cc(N3CCCNCC3)ccc2[nH]1]

orange powder, HPLC/MS 0.93 min, [M+H]$^+$434; $^1$H NMR (400 MHz, DMSO-d$_6$, TFA-d$_1$) δ 9.06 (d, J=2.6 Hz, 1H), 8.17 (d, J=2.7 Hz, 1H), 7.91-7.84 (m, 1H), 7.76 (d, J=9.0 Hz, 1H), 7.61 (m, 1H), 7.23 (t, J=9.2 Hz, 1H), 7.19-7.11 (m, 2H), 4.74 (s, 2H), 3.92-3.82 (m, 2H), 3.76-3.57 (m, 3H), 3.42 (t, J=5.0 Hz, 2H), 3.28-3.18 (m, 2H), 2.23 (m, 2H).

5-(3-Fluoro-4-hydroxymethyl-phenyl)-3-(5-piperazin-1-yl-1H-benzimidazol-2-yl)-1H-pyridin-2-one bistrifluoroacetate ("A25")

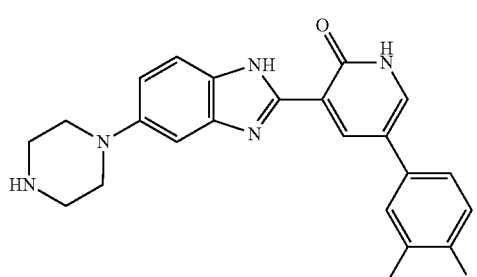

orange solid, HPLC/MS 0.90 min, [M+H]$^+$430; $^1$H NMR (400 MHz, DMSO-d$_6$, TFA-d$_1$) δ 9.10 (d, J=2.7 Hz, 1H), 8.37 (d, J=2.7 Hz, 1H), 7.84 (d, J=9.8 Hz, 1H), 7.67-7.56 (m, 3H), 7.43-7.32 (m, 2H), 4.66 (s, 2H), 3.50 (m, 4H), 3.43-3.33 (m, 4H).

3-[5-(4-Amino-piperidin-1-yl)-1H-benzimidazol-2-yl]-5-(3-hydroxymethyl-phenyl)-1H-pyridin-2-one dihydrochloride ("A26")

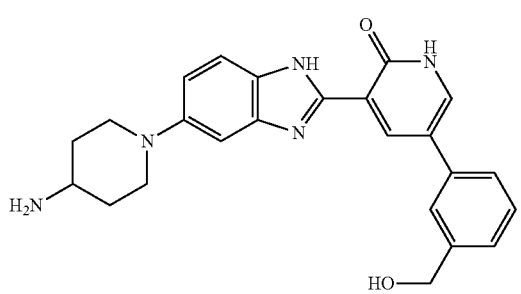 [SMILES: NC1CCN(c2ccc3[nH]c(-c4cc(-c5cccc(CO)c5)c[nH]c4=O)nc3c2)CC1]

orange solid, HPLC/MS 0.90 min, [M+H]$^+$416; $^1$H NMR (400 MHz, DMSO-d$_6$, TFA-d$_1$) $^1$H NMR (400 MHz, DMSO-d6) δ 9.15 (d, J=2.6 Hz, 1H), 8.28 (d, J=2.8 Hz, 1H), 7.95 (m, 2H), 7.70 (m, 2H), 7.60 (d, J=7.9 Hz, 1H), 7.44 (t, J=7.6 Hz, 1H), 7.34 (d, J=7.5 Hz, 1H), 4.59 (s, 2H), 3.79 (d, J=12.5 Hz, 2H), 3.45 (m, 3H), 2.19 (d, J=13.2 Hz, 2H), 2.03 (m, 2H).

5-(3-Hydroxymethyl-phenyl)-3-[5-(4-methyl-piperazin-1-yl)-1H-benzimidazol-2-yl]-1H-pyridin-2-one ("A27")

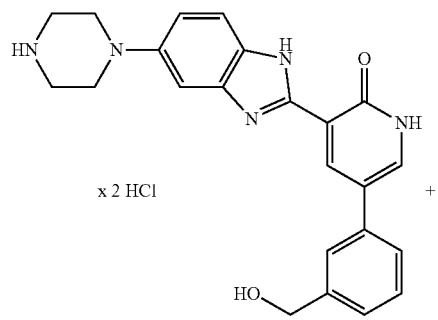

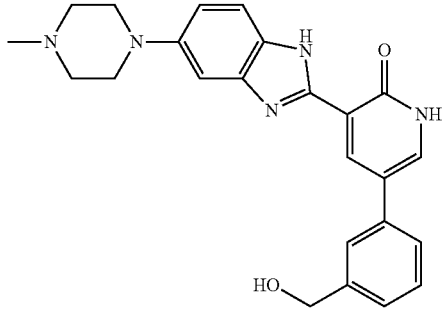

To a suspension of 5-(3-hydroxymethyl-phenyl)-3-(5-piperazin-1-yl-1H-benzimidazol-2-yl)-1H-pyridin-2-one dihydrochloride (94.9 mg, 0.20 mmol) and sodium carbonate (64 mg, 0.60 mmol) in acetonitrile (1 ml) is added formaldehyde (35% aqueous solution, 78 μl, 1.0 mmol). The mixture is stirred for five minutes at room temperature. Then, sodium cyanoborohydride (15.1 mg, 0.40 mmol) is added and the reaction mixture is stirred for 22 hours at room temperature. The reaction mixture is filtered and the filtrate is evaporated in vacuo. The residue is purified by preparative HPLC to afford 5-(3-hydroxymethyl-phenyl)-3-[5-(4-methyl-piperazin-1-yl)-1H-benzimidazol-2-yl]-1H-pyridin-2-one as yellow solid; HPLC/MS 0.93 min, [M+H]$^+$416; $^1$H NMR (400 MHz, DMSO-d$_6$, TFA-d$_1$) δ 9.08 (d, J=2.6 Hz, 1H), 8.29 (d, J=2.6 Hz, 1H), 8.12 (s, 1H), 7.84 (d, J=8.9 Hz, 1H), 7.73 (s, 1H), 7.63 (d, J=8.3 Hz, 1H), 7.49 (t, J=7.6 Hz, 1H), 7.40 (d, J=2.0 Hz, 1H), 7.38 (m, 2H), 4.65 (s, 2H), 3.94 (d, J=12.5 Hz, 2H), 3.65 (d, J=12.0 Hz, 2H), 3.30 (t, J=11.5 Hz, 2H), 3.15 (t, J=12.7 Hz, 2H), 2.95 (s, 3H).

The following compounds are prepared analogously

5-[5-(4-Methyl-piperazin-1-yl)-1H-benzimidazol-2-yl]-1H-[3,4']bipyridinyl-6-one ("A28")

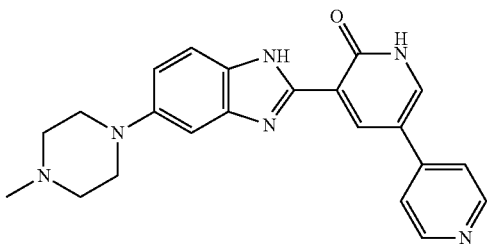 [SMILES: CN1CCN(c2ccc3[nH]c(-c4cc(-c5ccncc5)c[nH]c4=O)nc3c2)CC1]

MS-ESI: [M+H]$^+$387; $^1$H NMR (400 MHz, DMSO-d$_6$, TFA-d$_1$) δ 9.38 (d, J=2.7 Hz, 1H), 9.07-9.00 (m, 2H), 8.97 (dd, J=2.8, 1.4 Hz, 1H), 8.51 (d, J=7.1 Hz, 2H), 8.10 (d, J=1.2 Hz, 1H), 7.88 (d, J=9.0 Hz, 1H), 7.44 (d, J=2.2 Hz, 1H), 7.43-7.38 (m, 1H), 3.94 (d, J=13.0 Hz, 2H), 3.67 (d, J=12.0 Hz, 2H), 3.43-3.27 (m, 2H), 3.28-3.13 (m, 2H), 2.97 (s, 3H).

3-[5-(4-Methyl-piperazin-1-yl)-1H-benzimidazol-2-yl]-5-quinolin-4-yl-1H-pyridin-2-one ("A29")

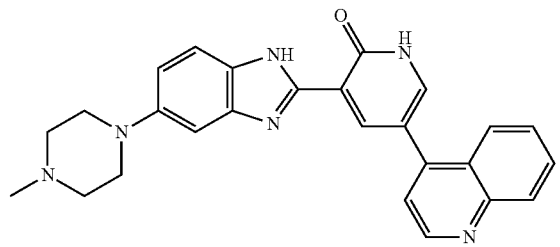 [SMILES: CN1CCN(c2ccc3[nH]c(-c4cc(-c5ccnc6ccccc56)c[nH]c4=O)nc3c2)CC1]

MS-ESI: [M+H]$^+$437; $^1$H NMR (400 MHz, DMSO-d$_6$, TFA-d$_1$) δ 9.47 (d, J=5.6 Hz, 1H), 8.97 (d, J=2.6 Hz, 1H), 8.46 (d, J=2.6 Hz, 1H), 8.44 (d, J=8.7 Hz, 1H), 8.40 (d, J=8.6 Hz, 1H), 8.23 (m, 2H), 8.00 (t, J=7.8 Hz, 1H), 7.80 (d, J=9.0 Hz, 1H), 7.39 (dd, J=9.2, 2.3 Hz, 1H), 7.30 (d, J=2.2 Hz, 1H), 3.91 (d, J=13.1 Hz, 2H), 3.60 (d, J=12.1 Hz, 2H), 3.25 (td, J=12.1, 2.9 Hz, 2H), 3.08 (t, J=11.8 Hz, 2H), 2.91 (s, 3H).

3-[5-(4-Methyl-piperazin-1-yl)-1H-benzimidazol-2-yl]-5-(1-methyl-1H-pyrazol-4-yl)-1H-pyridin-2-one ("A30")

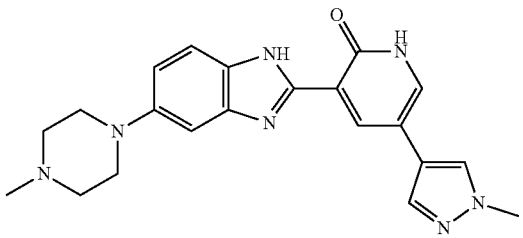

MS-ESI: [M+H]$^+$390; $^1$H NMR (400 MHz, DMSO-d$_6$, TFA-d$_1$) δ 8.95 (d, J=2.5 Hz, 1H), 8.23 (d, J=2.6 Hz, 1H), 8.11 (s, 1H), 7.89 (s, 1H), 7.84 (d, J=8.9 Hz, 1H), 7.47-7.34

(m, 2H), 3.92 (m, 5H), 3.64 (d, J=12.1 Hz, 2H), 3.37-3.21 (m, 2H), 3.19-3.06 (m, 2H), 2.94 (s, 3H).

5-[5-(4-Methyl-piperazin-1-yl)-1H-benzimidazol-2-yl]-1H-[3,3']bipyridinyl-6-one ("A31")

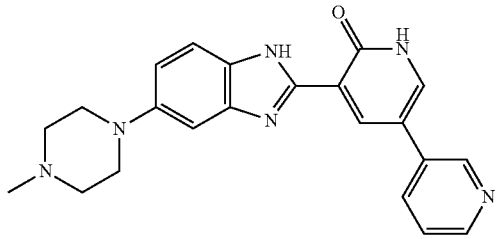 [SMILES: CN1CCN(c2ccc3[nH]c(-c4cc(-c5cccnc5)c[nH]c4=O)nc3c2)CC1]

MS-ESI: [M+H]⁺387.

3-[6-(4-Methyl-piperazin-1-yl)-1H-benzimidazol-2-yl]-5-(3-methyl-1H-pyrazol-4-yl)-1H-pyridin-2-on ("A32")

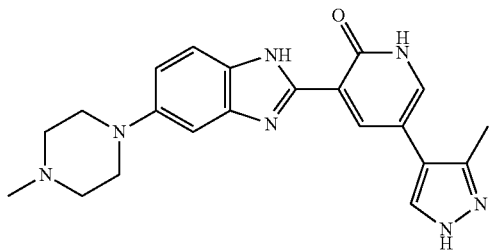

MS-ESI: [M+H]⁺390; ¹H NMR (400 MHz, DMSO-d₆, TFA-d₁) δ 8.79 (d, J=2.6 Hz, 1H), 8.12 (s, 1H), 8.06 (d, J=2.6 Hz, 1H), 7.83 (d, J=9.0 Hz, 1H), 7.40 (dd, J=9.1, 2.3 Hz, 1H), 7.37 (d, J=2.1 Hz, 1H), 3.93 (d, J=13.2 Hz, 2H), 3.69-3.59 (m, 2H), 3.29 (td, J=11.9, 3.0 Hz, 2H), 3.19-3.05 (m, 2H), 2.94 (s, 3H), 2.48 (s, 3H).

5-(3-Hydroxymethyl-phenyl)-3-[5-(4-methyl-[1,4]diazepan-1-yl)-1H-benzimidazol-2-yl]-1H-pyridin-2-one ("A33")

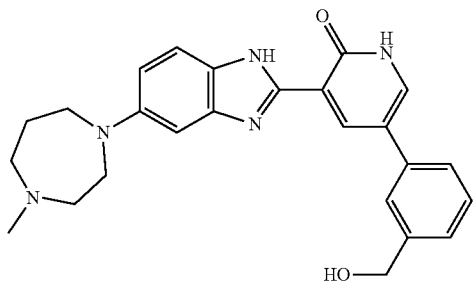 [SMILES: CN1CCCN(c2ccc3[nH]c(-c4cc(-c5cccc(CO)c5)c[nH]c4=O)nc3c2)CC1]

orange-brown solid, HPLC/MS 0.94 min, [M+H]⁺430; ¹H NMR (500 MHz, DMSO-d₆, TFA-d₁) δ 9.00 (d, J=2.6 Hz, 1H), 8.24 (d, J=2.6 Hz, 1H), 8.09 (s, 1H, formate), 7.74 (d, J=9.1 Hz, 1H), 7.68 (s, 1H), 7.59 (d, J=8.0 Hz, 1H), 7.45 (t, J=7.6 Hz, 1H), 7.35 (d, J=7.6 Hz, 1H), 7.13 (dd, J=9.2, 2.4 Hz, 1H), 7.03 (d, J=2.3 Hz, 1H), 4.60 (s, 2H), 3.89 (m, 1H), 3.75 (m, 1H), 3.66-3.45 (m, 4H), 3.31 (m, 1H), 3.26-3.17 (m, 1H), 2.88 (s, 3H), 2.23 (m, 2H).

5-(4-Fluoro-3-hydroxymethyl-phenyl)-3-[5-(4-methyl-piperazin-1-yl)-1H-benzimidazol-2-yl]-1H-pyridin-2-one ("A34")

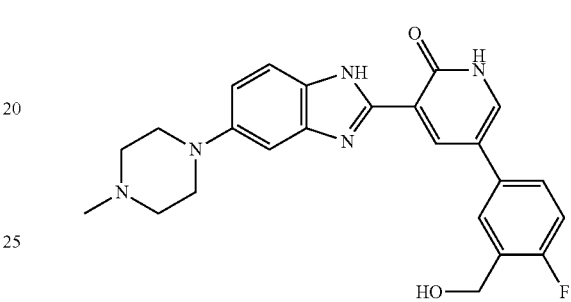

yellow solid, HPLC/MS 0.95 min, [M+H]⁺434; ¹H NMR (400 MHz, DMSO-d₆, TFA-d₁) δ 9.06 (d, J=2.7 Hz, 1H), 8.26 (d, J=2.6 Hz, 1H), 8.12 (s, 1H, formate), 7.87 (dd, J=7.0, 2.5 Hz, 1H), 7.84 (d, J=8.9 Hz, 1H), 7.66 (ddd, J=7.9, 4.8, 2.6 Hz, 1H), 7.43-7.35 (m, 2H), 7.28 (dd, J=9.8, 8.5 Hz, 1H), 4.70 (s, 2H), 3.94 (d, J=13.1 Hz, 2H), 3.65 (d, J=12.0 Hz, 2H), 3.41-3.23 (m, 2H), 3.25-3.09 (m, 2H) 2.96 (s, 3H).

5-(4-Hydroxymethyl-phenyl)-3-[5-(4-methyl-piperazin-1-yl)-1H-benzimidazol-2-yl]-1H-pyridin-2-one ("A35")

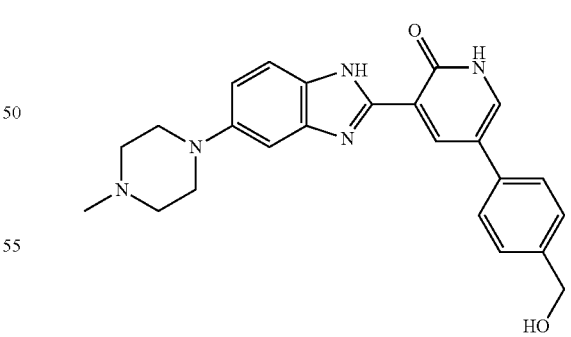

yellow solid, HPLC/MS 0.92 min, [M+H]⁺416; ¹H NMR (400 MHz, DMSO-d₆, TFA-d₁) δ 9.10 (d, J=2.7 Hz, 1H), 8.29 (d, J=2.6 Hz, 1H), 7.84 (d, J=9.8 Hz, 1H), 7.73 (d, J=8.3 Hz, 2H), 7.50 (d, J=8.1 Hz, 2H), 7.43-7.33 (m, 2H), 4.61 (s, 2H), 3.94 (d, J=13.1 Hz, 2H), 3.65 (d, J=12.0 Hz, 2H), 3.31 (t, J=11.4 Hz, 2H), 3.16 (t, J=12.3 Hz, 2H), 2.96 (s, 3H).

3-[5-(4-Dimethylamino-piperidin-1-yl)-1H-benzimidazol-2-yl]-5-(3-hydroxymethyl-phenyl)-1H-pyridin-2-one formate ("A36")

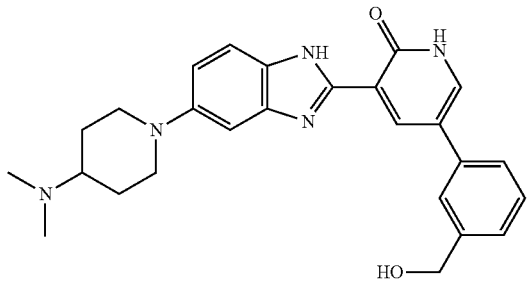 [SMILES: CN(C)C1CCN(c2ccc3[nH]c(-c4cc(-c5cccc(CO)c5)c[nH]c4=O)nc3c2)CC1]

yellow solid, HPLC/MS 0.92 min, [M+H]⁺445; ¹H NMR (400 MHz, DMSO-d₆, TFA-d₁) δ 9.03 (d, J=2.7 Hz, 1H), 8.27 (d, J=2.6 Hz, 1H), 8.11 (s, 1H, formate), 7.80 (d, J=8.9 Hz, 1H), 7.69 (t, J=1.7 Hz, 1H), 7.60 (dt, J=7.8, 1.5 Hz, 1H), 7.46 (t, J=7.6 Hz, 1H), 7.43-7.30 (m, 3H), 4.61 (s, 2H), 3.91 (d, J=12.7 Hz, 2H), 3.40 (ddt, J=11.8, 7.4, 3.7 Hz, 1H), 3.04-2.87 (m, 2H), 2.82 (s, 6H), 2.17 (d, J=11.2 Hz, 2H), 1.82 (qd, J=12.1, 4.0 Hz, 2H).

5-(2-Fluoro-3-hydroxymethyl-phenyl)-3-[5-(4-methyl-piperazin-1-yl)-1H-benzimidazol-2-yl]-1H-pyridin-2-one trifluoroacetate ("A37")

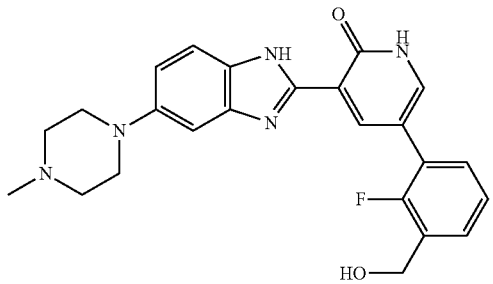 [SMILES: CN1CCN(c2ccc3[nH]c(-c4cc(-c5cccc(CO)c5F)c[nH]c4=O)nc3c2)CC1]

yellow solid, HPLC/MS 0.90 min, [M+H]⁺434; ¹H NMR (400 MHz, DMSO-d₆, TFA-d₁) δ 8.94 (d, J=2.6 Hz, 1H), 8.17 (d, J=2.6 Hz, 1H), 7.82 (d, J=9.0 Hz, 1H), 7.57 (m, 2H), 7.45-7.26 (m, 3H), 4.69 (s, 2H), 3.93 (d, J=13.4 Hz, 2H), 3.65 (d, J=11.6 Hz, 2H), 3.43-3.25 (m, 2H), 3.23-3.05 (m, 2H), 2.95 (s, 3H).

3-[5-(4-Hydroxy-piperidin-1-yl)-1H-benzimidazol-2-yl]-5-(1H-pyrrolo[2,3-b]-pyridin-4-yl)-1H-pyridin-2-one ("A38")

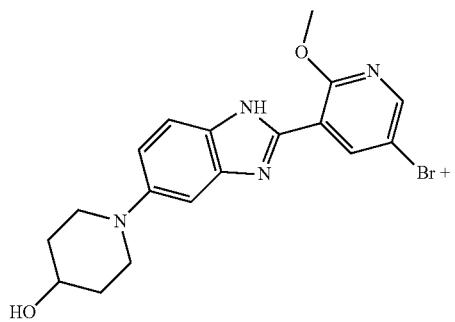

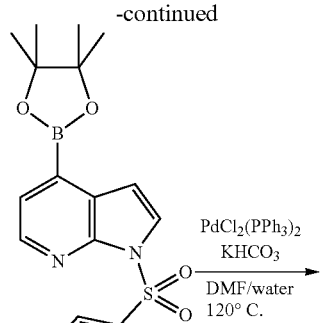

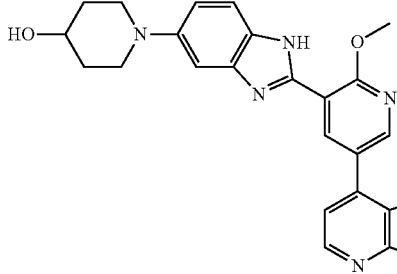

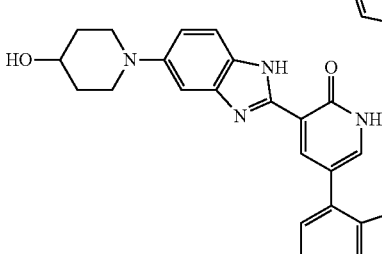

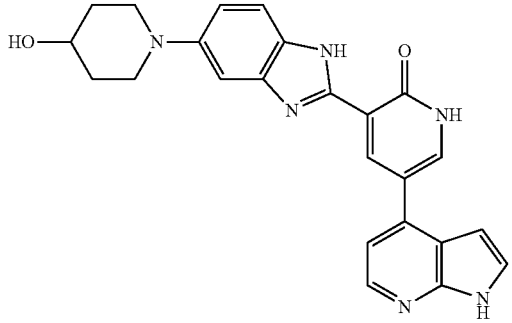

A microwave vial is charged with 1-[2-(5-bromo-2-methoxy-pyridin-3-yl)-1H-benzimidazol-5-yl]-piperidin-4-ol (371 mg, 0.92 mmol), 1-phenylsulfonyl-1H-pyrrolo[2,3-b]pyridine-4-boronic acid pinacol ester (368 mg, 0.96 mmol), potassium hydrogen carbonate (122 mg, 1.22 mmol), DMF (2.0 ml) and water (0.4 ml). The vial is flushed with nitrogen Then, bis(triphenylphosphine)-palladium(II) chloride (13 mg, 18 μmol) is added under nitrogen and the reaction mixture is irradiated in a microwave reactor for 1 hour at 120° C. The reaction mixture is poured into water (20 ml), the resultant precipitate is filtered off and washed with water. The residue is chromatographed on a silica gel column with dichloromethane/methanol as eluent to afford 1-{2-[5-(1-benzenesulfonyl-1H-pyrrolo[2,3-b]pyridin-4-yl)-2-methoxy-pyridin-3-yl]-1H-benzimidazol-5-yl}-piperidin-4-ol as yellow solid; HPLC/MS 1.22 min, [M+H]$^+$581; $^1$H NMR (500 MHz, DMSO-d$_6$) δ 8.89 (d, J=2.4 Hz, 1H), 8.86 (d, J=2.4 Hz, 1H), 8.51 (d, J=5.0 Hz, 1H), 8.23-8.13 (m, 2H), 8.05 (m, 2H), 8.01 (d, J=9.0 Hz, 1H), 7.81 (dd, J=9.0, 2.2 Hz, 1H), 7.75-7.67 (m, 1H), 7.67-7.58 (m, 2H), 7.55 (d, J=5.1 Hz, 1H), 7.12 (d, J=4.1 Hz, 1H), 4.23 (s, 3H), 3.94 (tt, J=7.5, 3.6 Hz, 1H), 3.77 (ddd, J=11.2, 7.7, 4.4 Hz, 2H), 3.57 (ddd, J=11.7, 8.2, 3.4 Hz, 2H), 2.21-2.06 (m, 2H), 1.87 (m, 2H).

A microwave vial is charged with 1-{2-[5-(1-benzenesulfonyl-1H-pyrrolo[2,3-b]-pyridin-4-yl)-2-methoxy-pyridin-3-yl]-1H-benzimidazol-5-yl}-piperidin-4-ol (308 mg, 0.53 mmol), water (1.8 ml) and aqueous hydrochloric acid (37% by weight, 1.8 ml). The vial is irradiated in the microwave reactor for 15 minutes at 100° C. The reaction mixture is poured into 30 ml 1 N NaOH solution. The resultant precipitate is filtered off, washed with water and dried under vacuum to afford 5-(1-benzenesulfonyl-1H-pyrrolo[2,3-b]pyridin-4-yl)-3-[5-(4-hydroxy-piperidin-1-yl)-1H-benzimidazol-2-yl]-1H-pyridin-2-one as brown solid; HPLC/MS 1.10 min, [M+H]$^+$567; $^1$H NMR (500 MHz, DMSO-d$_6$, TFA-d$_1$) δ 9.06 (d, J=2.6 Hz, 1H), 8.47 (d, J=5.0 Hz, 1H), 8.37 (d, J=2.6 Hz, 1H), 8.22 (d, J=2.1 Hz, 1H), 8.19-8.13 (m, 2H), 8.05 (d, J=9.0 Hz, 1H), 8.02 (d, J=4.1 Hz, 1H), 7.89 (dd, J=9.0, 2.2 Hz, 1H), 7.69 (t, J=7.5 Hz, 1H), 7.60 (t, J=7.9 Hz, 2H), 7.49 (d, J=5.0 Hz, 1H), 7.09 (d, J=4.1 Hz, 1H), 3.96 (tt, J=7.3, 3.5 Hz, 1H), 3.76 (ddd, J=11.3, 7.4, 3.7 Hz, 2H), 3.61 (ddd, J=11.6, 7.8, 3.6 Hz, 2H), 2.15 (ddt, J=14.2, 6.9, 3.5 Hz, 2H), 1.92 (dtd, J=14.1, 7.7, 3.6 Hz, 2H).

To a suspension of 5-(1-benzenesulfonyl-1H-pyrrolo[2,3-b]pyridin-4-yl)-3-[5-(4-hydroxy-piperidin-1-yl)-1H-benzimidazol-2-yl]-1H-pyridin-2-one (153 mg, 0.27 mmol) and cesium carbonate (259 mg, 0.80 mmol) in THF (500 μl) is added 2,2,2-trifluoroethanol (500 μl) and the reaction mixture is stirred for 2 hours at 80° C. The reaction mixture is concentrated under reduced pressure and the residue is chromatographed on a silica gel column to afford 3-[5-(4-hydroxy-piperidin-1-yl)-1H-benzimidazol-2-yl]-5-(1H-pyrrolo[2,3-b]pyridin-4-yl)-1H-pyridin-2-one as yellow solid; HPLC/MS 0.92 min, [M+H]$^+$427; $^1$H NMR (400 MHz, DMSO-d$_6$, TFA-d$_1$) δ 9.22 (d, J=2.7 Hz, 1H), 8.61 (d, J=1.7 Hz, 1H), 8.60 (d, J=1.9 Hz, 1H), 8.21 (d, J=2.1 Hz, 1H), 8.07 (d, J=9.0 Hz, 1H), 7.92-7.84 (m, 2H), 7.77 (d, J=6.3 Hz, 1H), 7.15 (d, J=3.6 Hz, 1H), 3.97 (tt, J=7.1, 3.4 Hz, 1H), 3.78 (ddd, J=11.4, 7.7, 3.6 Hz, 2H), 3.61 (ddd, J=11.7, 7.6, 3.6 Hz, 2H), 2.15 (ddd, J=14.3, 7.3, 3.7 Hz, 2H), 1.91 (m, 2H).

The following compounds are prepared analogously 3-(1H-Benzimidazol-2-yl)-5-(1H-pyrrolo[2,3-b]pyridin-4-yl)-1H-pyridin-2-one ("A39")

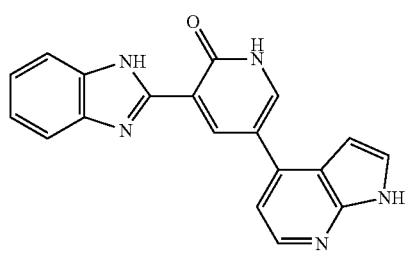 [SMILES: O=c1[nH]cc(-c2ccnc3[nH]ccc23)cc1-c1nc2ccccc2[nH]1]

MS-ESI: [M+H]$^+$328; $^1$H NMR (400 MHz, DMSO-d$_6$) δ 13.40 (bs, 1H), 11.96 (s, 1H), 9.09 (d, J=2.6 Hz, 1H), 8.41-8.29 (m, 2H), 7.90 (m, 2H), 7.66-7.62 (m, 1H), 7.54 (m, 2H), 7.31 (d, J=5.0 Hz, 1H), 6.81-6.75 (m, 1H).

3-[5-(Pyridin-4-yloxy)-1H-benzimidazol-2-yl]-5-(1H-pyrrolo[2,3-b]pyridin-4-yl)-1H-pyridin-2-one ("A40")

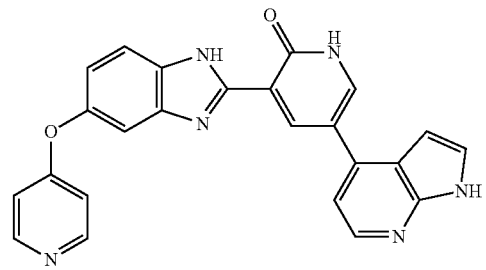 [SMILES: O=c1[nH]cc(-c2ccnc3[nH]ccc23)cc1-c1nc2cc(Oc3ccncc3)ccc2[nH]1]

MS-ESI: [M+H]$^+$421.

3-(5-Morpholin-4-yl-1H-benzimidazol-2-yl)-5-(1H-pyrrolo[2,3-b]pyridin-4-yl)-1H-pyridin-2-one ("A41")

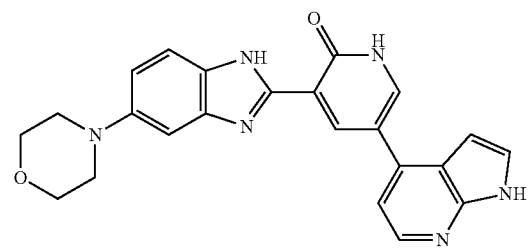 [SMILES: O=c1[nH]cc(-c2ccnc3[nH]ccc23)cc1-c1nc2cc(N3CCOCC3)ccc2[nH]1]

HPLC/MS 0.97 min, [M+H]$^+$413; $^1$H NMR (400 MHz, DMSO-d$_6$, TFA-d$_1$) δ 9.13 (d, J=2.6 Hz, 1H), 8.60 (d, J=6.3 Hz, 1H), 8.54 (d, J=2.6 Hz, 1H), 7.86 (d, J=3.6 Hz, 1H), 7.82 (d, J=9.8 Hz, 1H), 7.75 (d, J=6.3 Hz, 1H), 7.50-7.37 (m, 2H), 7.15 (d, J=3.6 Hz, 1H), 3.87-3.79 (m, 4H), 3.45-3.23 (m, 4H).

3-(5-Methoxy-1H-benzimidazol-2-yl)-5-(1H-pyrrolo[2,3-b]pyridin-4-yl)-1H-pyridin-2-one ("A42")

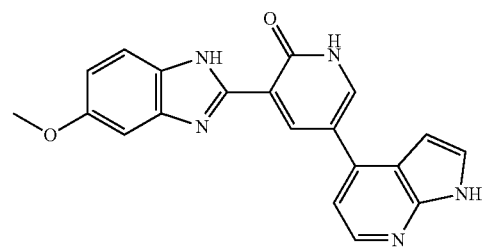 [SMILES: COc1ccc2[nH]c(-c3cc(-c4ccnc5[nH]ccc45)c[nH]c3=O)nc2c1]

MS-ESI: [M+H]$^+$358; $^1$H NMR (400 MHz, DMSO-d$_6$, TFA-d$_1$) δ 9.12 (d, J=2.6 Hz, 1H), 8.53 (d, J=6.3 Hz, 1H), 8.47 (d, J=2.6 Hz, 1H), 7.78 (d, J=3.6 Hz, 1H), 7.74 (d, J=9.1

Hz, 1H), 7.70 (d, J=6.3 Hz, 1H), 7.30 (d, J=2.4 Hz, 1H), 7.15-7.07 (m, 2H), 3.81 (s, 3H).

3-(5-Piperidin-1-yl-1H-benzimidazol-2-yl)-5-(1H-pyrrolo[2,3-b]pyridin-4-yl)-1H-pyridin-2-one ("A43")

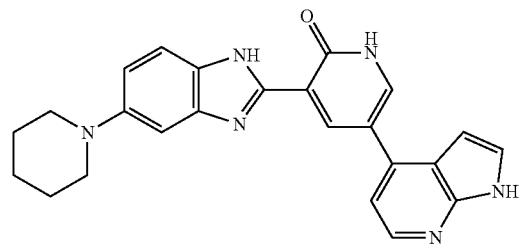 [SMILES: O=c1[nH]cc(-c2ccnc3[nH]ccc23)cc1-c1nc2cc(N3CCCCC3)ccc2[nH]1]

HPLC/MS 1.01 min, [M+H]⁺411; ¹H NMR (400 MHz, DMSO-d₆, TFA-d₁) δ 9.23 (d, J=2.7 Hz, 1H), 8.55 (d, J=2.7 Hz, 1H), 8.53 (d, J=6.2 Hz, 1H), 8.26 (d, J=2.1 Hz, 1H), 8.06 (d, J=9.0 Hz, 1H), 7.89 (dd, J=9.0, 2.2 Hz, 1H), 7.78 (d, J=3.6 Hz, 1H), 7.72 (d, J=6.3 Hz, 1H), 7.10 (d, J=3.6 Hz, 1H), 3.63 (t, J=5.5 Hz, 4H), 1.96 (m, 4H), 1.78-1.63 (m, 2H).

3-(5-Piperazin-1-yl-1H-benzimidazol-2-yl)-5-(1H-pyrrolo[2,3-b]pyridin-4-yl)-1H-pyridin-2-one dihydrochloride ("A44")

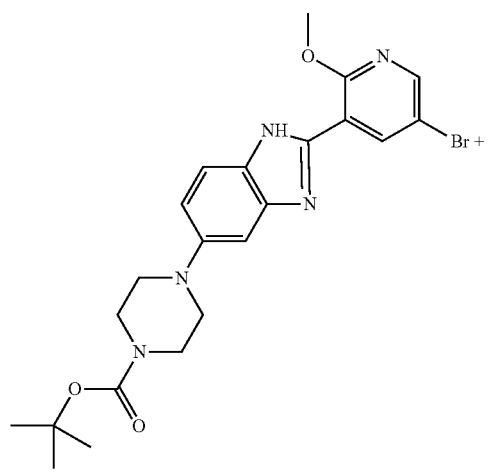

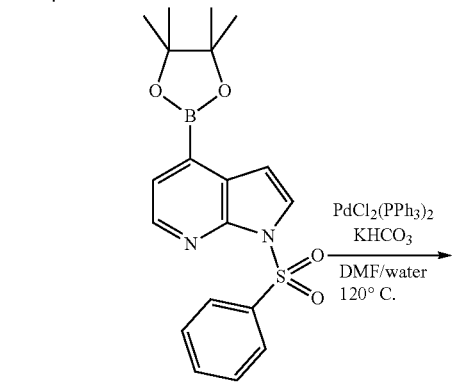

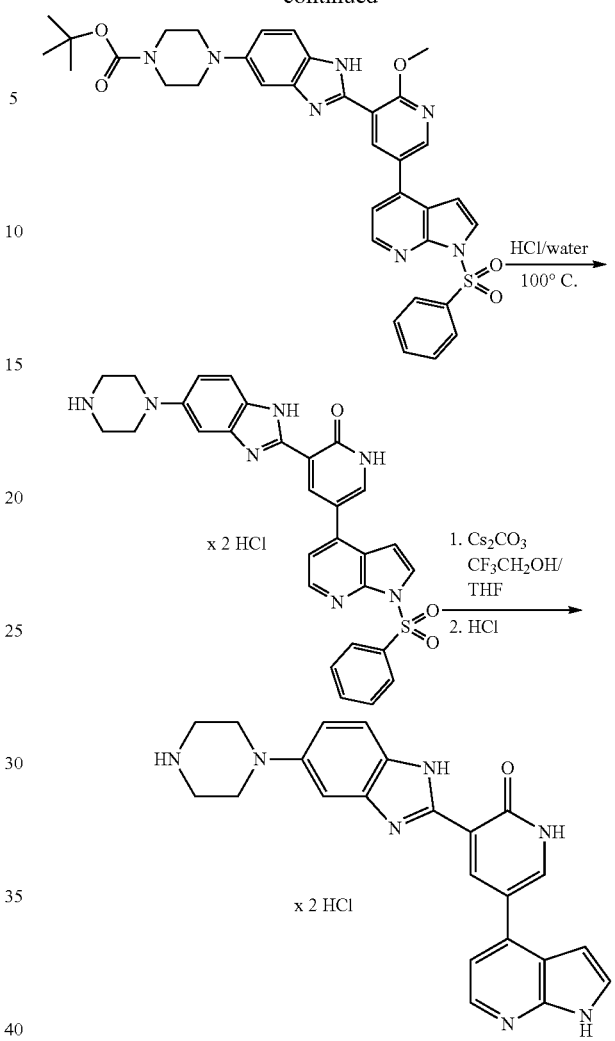

A microwave vial is charged with 4-[2-(5-bromo-2-methoxy-pyridin-3-yl)-1H-benzimidazol-5-yl]-piperazine-1-carboxylic acid tert-butyl ester (464 mg, 0.95 mmol), 1-phenylsulfonyl-1H-pyrrolo[2,3-b]pyridine-4-boronic acid pinacol ester (588 mg, 1.53 mmol), potassium hydrogen carbonate (125 mg, 1.25 mmol), DMF (2.4 ml) and water (1.2 ml). The vial is flushed with nitrogen. Then, bis (triphenylphosphine)palladium(II) chloride (42 mg, 0.06 mmol) is added under nitrogen and the reaction mixture is irradiated in a microwave reactor for 2 hours at 120° C. The reaction mixture is filtered over kieselguhr and the filtrate is concentrated in vacuo. The residue is chromatographed on a silica gel column with dichloromethane/methanol as eluent to afford 4-{2-[5-(1-benzenesulfonyl-1H-pyrrolo[2,3-b]pyridin-4-yl)-2-methoxy-pyridin-3-yl]-1H-benzimidazol-5-yl}-piperazine-1-carboxylic acid tert-butyl ester as beige amorphous solid; HPLC/MS 2.82 min, [M+H]⁺666; ¹H NMR (500 MHz, DMSO-d₆, TFA-d₁) δ 8.84 (d, J=2.3 Hz, 1H), 8.79 (d, J=2.3 Hz, 1H), 8.48 (d, J=5.0 Hz, 1H), 8.20-8.12 (m, 2H), 7.98 (d, J=4.1 Hz, 1H), 7.76 (d, J=9.0 Hz, 1H), 7.67-7.62 (m, 1H), 7.55 (m, 2H), 7.48 (d, J=5.0 Hz, 1H), 7.42 (dd, J=9.1, 2.3 Hz, 1H), 7.34 (d, J=2.2 Hz, 1H), 7.06 (d, J=4.1 Hz, 1H), 4.21 (s, 3H), 3.57 (t, J=5.1 Hz, 4H), 3.28 (t, J=5.2 Hz, 4H), 1.39 (s, 9H).

A microwave vial is charged with 4-{2-[5-(1-benzenesulfonyl-1H-pyrrolo[2,3-b]-pyridin-4-yl)-2-methoxy-pyridin-3-yl]-1H-benzimidazol-5-yl}-piperazine-1-carboxylic acid tert-butyl ester (266 mg, 0.40 mmol), water (1.5 ml) and aqueous hydrochloric acid (37% by weight, 1.5 ml). The vial is irradiated in the microwave reactor for 30 minutes at 100° C. The reaction mixture is poured into 30 ml 1 N NaOH solution. The resultant precipitate is evaporated to afford 5-(1-benzenesulfonyl-1H-pyrrolo[2,3-b]pyridin-4-yl)-3-(5-piperazin-1-yl-1H-benzimidazol-2-yl)-1H-pyridin-2-one dihydrochloride as beige solid; HPLC/MS 1.05 min, [M+H]$^+$552.

To a suspension of 5-(1-benzenesulfonyl-1H-pyrrolo[2,3-b]pyridin-4-yl)-3-(5-piperazin-1-yl-1H-benzimidazol-2-yl)-1H-pyridin-2-one dihydrochloride (50 mg, 0.08 mmol) and cesium carbonate (200 mg, 0.61 mmol) in THF (1 ml) is added 2,2,2-trifluoroethanol (1 ml) and the reaction mixture is stirred for 45 hours at 80° C. The reaction mixture is concentrated under reduced pressure and the residue is purified by preparative HPLC. The product containing fractions are combined and evaporated. The residue is dissolved in 2 N HCl (1 ml) and stirred for 2 hours at 80° C. The solution is evaporated and the residue is dried under vacuum to afford on a silica gel column to afford 3-(5-piperazin-1-yl-1H-benzimidazol-2-yl)-5-(1H-pyrrolo[2,3-b]pyridin-4-yl)-1H-pyridin-2-one dihydrochloride as orange fine powder; HPLC/MS 0.87 min, [M+H]$^+$412.

$^1$H NMR (400 MHz, DMSO-d$_6$) δ 16 (bs, 2H), 12.37 (s, 1H), 11.87 (s, 1H), 9.9 (bs, 2H), 9.01 (d, J=2.7 Hz, 1H), 8.30 (d, J=4.9 Hz, 1H), 8.06 (d, J=2.7 Hz, 1H), 7.61 (dd, J=3.5, 2.5 Hz, 1H), 7.57 (d, J=8.9 Hz, 1H), 7.26 (d, J=5.0 Hz, 1H), 7.23 (s, 1H), 7.00 (dd, J=8.9, 2.4 Hz, 1H), 6.65 (dd, J=3.6, 1.7 Hz, 1H), 3.34-3.23 (m, 4H), 3.22-3.13 (m, 4H).

The following compounds are prepared analogously 5-(2-Methyl-1H-pyrrolo[2,3-b]pyridin-3-yl)-3-(5-piperazin-1-yl-1H-benzimidazol-2-yl)-1H-pyridin-2-one ("A45")

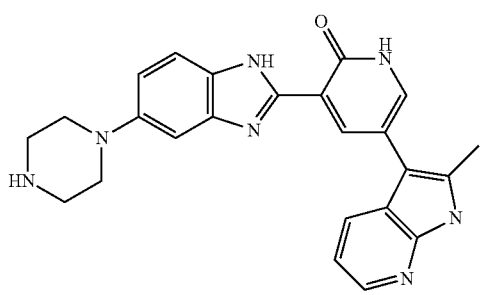 [SMILES: Cc1[nH]c2ncccc2c1-c1c[nH]c(=O)c(-c2nc3cc(N4CCNCC4)ccc3[nH]2)c1]

HPLC/MS 0.89 min, [M+H]$^+$426; $^1$H NMR (400 MHz, DMSO-d$_6$, TFA-d$_1$) δ 8.95 (d, J=2.5 Hz, 1H), 8.68 (dd, J=7.9, 1.2 Hz, 1H), 8.49 (dd, J=5.9, 1.2 Hz, 1H), 8.06 (d, J=2.5 Hz, 1H), 7.84 (d, J=9.0 Hz, 1H), 7.60 (dd, J=7.9, 5.9 Hz, 1H), 7.40 (d, J=2.2 Hz, 1H), 7.36 (dd, J=9.1, 2.3 Hz, 1H), 3.52 (dd, J=7.0, 3.6 Hz, 4H), 3.45-3.31 (m, 4H), 2.67 (s, 3H).

3-[6-(3,8-Diaza-bicyclo[3.2.1]oct-3-yl)-1H-benzimidazol-2-yl]-5-(1H-pyrrolo-[2,3-b]pyridin-4-yl)-1H-pyridin-2-one ("A46")

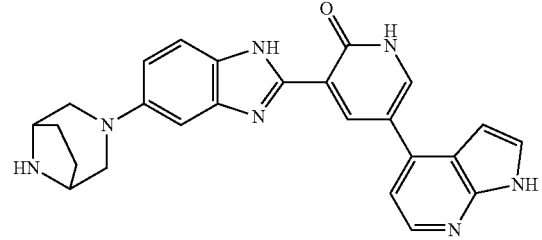 [SMILES: O=c1[nH]cc(-c2ccnc3[nH]ccc23)cc1-c1nc2cc(N3CC4CCC(C3)N4)ccc2[nH]1]

brown solid, HPLC/MS 0.93 min, [M+H]$^+$438; $^1$H NMR (400 MHz, DMSO-d$_6$) δ 9.20 (d, J=2.6 Hz, 1H), 8.67 (d, J=6.2 Hz, 1H), 8.60 (d, J=2.6 Hz, 1H), 7.92 (d, J=3.6 Hz, 1H), 7.84 (d, J=5.0 Hz, 1H), 7.82 (d, J=2.2 Hz, 1H), 7.35 (dd, J=9.2, 2.3 Hz, 1H), 7.29 (d, J=2.2 Hz, 1H), 7.22 (d, J=3.7 Hz, 1H), 4.26 (s, 2H), 3.76 (d, J=11.2 Hz, 2H), 3.27 (d, J=11.8 Hz, 2H), 2.09 (s, 4H).

3-(5-[1,4]Diazepan-1-yl-1H-benzimidazol-2-yl)-5-(1H-pyrrolo[2,3-b]pyridin-4-yl)-1H-pyridin-2-one ("A47")

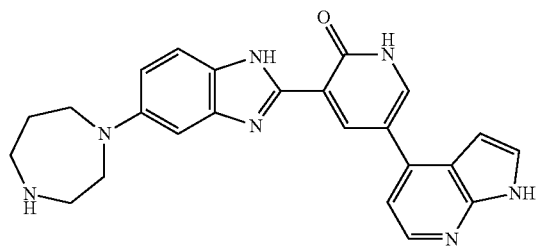 [SMILES: O=c1[nH]cc(-c2ccnc3[nH]ccc23)cc1-c1nc2cc(N3CCCNCC3)ccc2[nH]1]

light brown solid, HPLC/MS 0.93 min, [M+H]$^+$426; $^1$H NMR (400 MHz, DMSO-d$_6$, TFA-d$_1$) δ 9.10 (d, J=2.6 Hz, 1H), 8.57 (d, J=6.3 Hz, 1H), 8.49 (d, J=2.6 Hz, 1H), 7.82 (d, J=3.6 Hz, 1H), 7.73 (d, J=6.3 Hz, 1H), 7.71 (d, J=9.2 Hz, 1H), 7.14-7.09 (m, 2H), 7.04 (d, J=2.3 Hz, 1H), 3.79 (t, J=5.0 Hz, 2H), 3.58 (t, J=6.1 Hz, 2H), 3.38-3.27 (m, 2H), 3.16 (dd, J=6.6, 4.3 Hz, 2H), 2.14 (p, J=5.9 Hz, 2H).

5-(1H-Indol-4-yl)-3-(5-piperazin-1-yl-1H-benzimidazol-2-yl)-1H-pyridin-2-one ("A48")

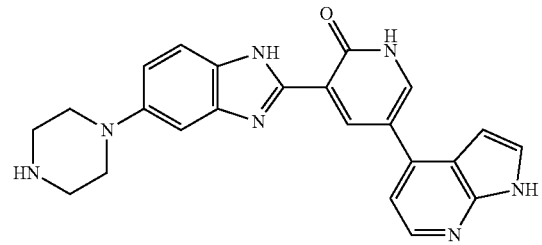 [SMILES: O=c1[nH]cc(-c2ccnc3[nH]ccc23)cc1-c1nc2cc(N3CCNCC3)ccc2[nH]1]

olive-yellow solid, HPLC/MS 0.97 min, [M+H]$^+$411; $^1$H NMR (400 MHz, DMSO-d$_6$, TFA-d$_1$) δ 9.00 (d, J=2.6 Hz, 1H), 8.03 (d, J=2.6 Hz, 1H), 7.66 (d, J=8.9 Hz, 1H), 7.41 (d, J=8.0 Hz, 1H), 7.30 (s, 1H), 7.24-7.12 (m, 3H), 7.08 (d, J=7.2 Hz, 1H), 3.37 (m, 4H), 3.24 (m, 4H).

5-(2-Methyl-1H-pyrrolo[2,3-b]pyridin-4-yl)-3-(5-piperazin-1-yl-1H-benzimidazol-2-yl)-1H-pyridin-2-one ("A48a")

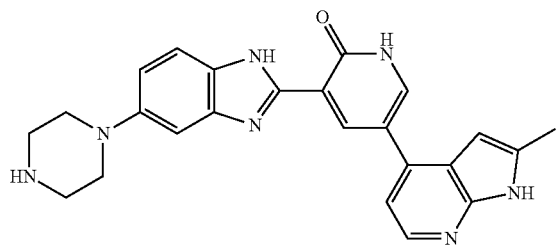 [SMILES: Cc1cc2c(-c3c[nH]c(=O)c(-c4nc5cc(N6CCNCC6)ccc5[nH]4)c3)ccnc2[nH]1]

$^1$H NMR (400 MHz, DMSO-d$_6$, TFA-d$_1$) δ 9.10 (d, J=2.7 Hz, 1H), 8.47 (d, J=2.6 Hz, 1H), 8.44 (d, J=6.3 Hz, 1H), 7.77 (d, J=9.7 Hz, 1H), 7.67 (d, J=6.3 Hz, 1H), 7.34-7.25 (m, 2H), 6.82 (s, 1H), 3.40-3-45 (m, 4H), 3.27-3.32 (m, 4H), 2.51 (s, 3H).

3-[5-(4-Methyl-[1,4]diazepan-1-yl)-1H-benzimidazol-2-yl]-5-(1H-pyrrolo-[2,3-b]pyridin-4-yl)-1H-pyridin-2-one ("A49")

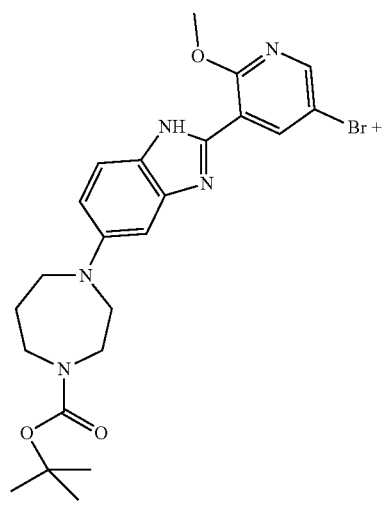

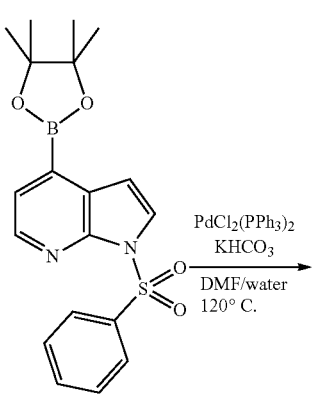

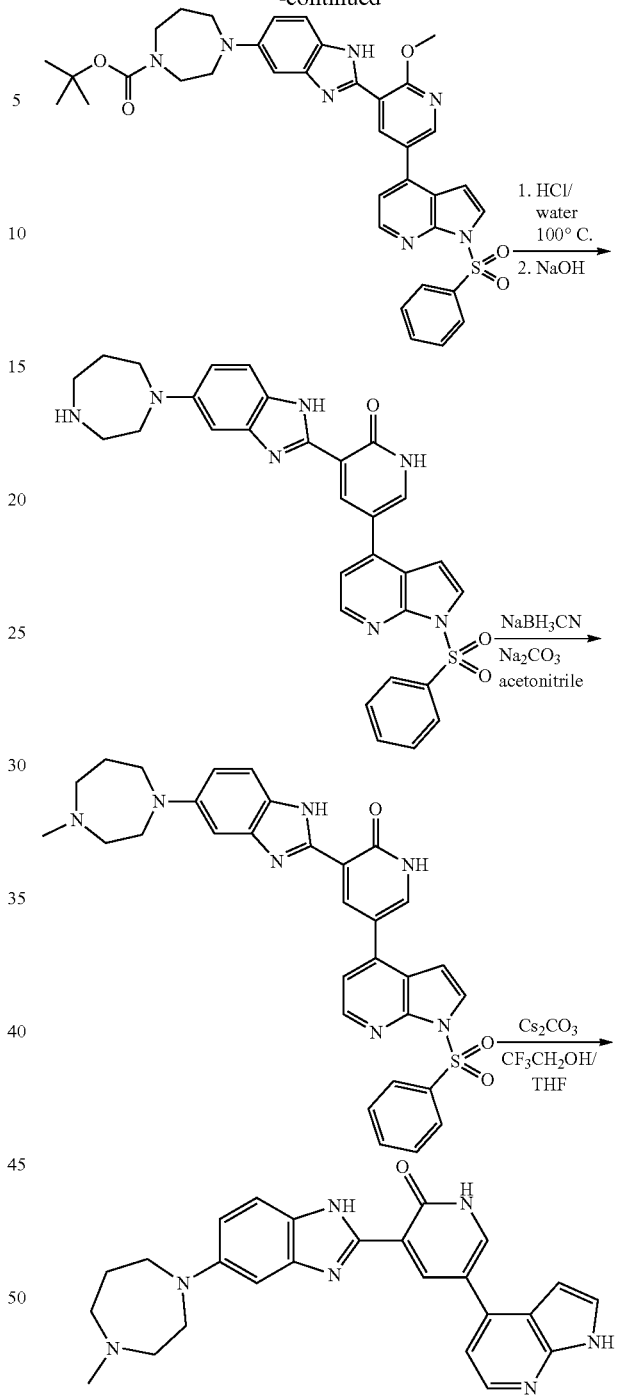

A microwave vial is charged with 4-[2-(5-bromo-2-methoxy-pyridin-3-yl)-1H-benzimidazol-5-yl]-[1,4]diazepane-1-carboxylic acid tert-butyl ester (502 mg, 1.00 mmol), 1-phenylsulfonyl-1H-pyrrolo[2,3-b]pyridine-4-boronic acid pinacol ester (500 mg, 1.30 mmol), sodium hydrogen carbonate (119 mg, 1.42 mmol), DMF (4.7 ml) and water (1.2 ml). The vial is flushed with nitrogen. Then, bis(triphenylphosphine)palladium(II) chloride (17 mg, 0.02 mmol) is added under nitrogen and the reaction mixture is irradiated in a microwave reactor for 30 minutes at 120° C. The reaction mixture is poured into water (80 ml) and the resultant precipitate is filtered off, washed with water and dried under vacuum. The residue filtered over kieselguhr and the filtrate is concentrated in vacuo. The residue is chromatographed on a silica gel column with cyclohexane/ethyl acetate as eluent to afford 4-{2-[5-(1-benzenesulfonyl-1H-pyrrolo[2,3-b]pyridin-4-yl)-2-methoxy-pyridin-3-yl]-1H-benzimidazol-5-yl}-[1,4]diazepane-1-carboxylic acid tert-butyl ester as yellow wax; HPLC/MS 1.45 min, [M+H]$^+$680.

In a reaction vial, 4-{2-[5-(1-benzenesulfonyl-1H-pyrrolo[2,3-b]pyridin-4-yl)-2-methoxy-pyridin-3-yl]-1H-benzimidazol-5-yl}-[1,4]diazepane-1-carboxylic acid tert-butyl ester (680 mg, 1.00 mmol) is suspended in water (2.5 ml) and aqueous hydrochloric acid (37% by weight, 2.5 ml). The reaction mixture is stirred for 2 hours at 80° C. The reaction mixture is cooled to room temperature and is made alkaline with 2 N NaOH solution. The resulting precipitate is filtered off, washed with water and dried under vacuum to afford 5-(1-benzenesulfonyl-1H-pyrrolo[2,3-b]pyridin-4-yl)-3-(5-[1,4]diazepan-1-yl-1H-benzimidazol-2-yl)-1H-pyridin-2-one as yellow crystals, HPLC/MS 1.06 min, [M+H]$^+$566.

To a suspension of 5-(1-benzenesulfonyl-1H-pyrrolo[2,3-b]pyridin-4-yl)-3-(5-[1,4]diazepan-1-yl-1H-benzimidazol-2-yl)-1H-pyridin-2-one (356 mg, 0.63 mmol) and sodium carbonate (66.9 mg, 0.63 mmol) in acetonitrile (5 ml) is added formaldehyde (35% aqueous solution, 248 μl, 3.2 mmol). The mixture is stirred for five minutes at room temperature. Then, sodium cyanoborohydride (97.3 mg, 1.26 mmol) is added and the reaction mixture is stirred for 42 hours at room temperature. The reaction mixture is evaporated and the residue is treated with saturated sodium hydrogen carbonate solution. The resultant precipitate is filtered off, washed with water and dried under vacuum to afford 5-(1-benzenesulfonyl-1H-pyrrolo[2,3-b]pyridin-4-yl)-3-[5-(4-methyl-[1,4]diazepan-1-yl)-1H-benzimidazol-2-yl]-1H-pyridin-2-one as brown solid; HPLC/MS 1.07 min, [M+H]$^+$580.

To a solution of 5-(1-benzenesulfonyl-1H-pyrrolo[2,3-b]pyridin-4-yl)-3-[5-(4-methyl-[1,4]diazepan-1-yl)-1H-benzimidazol-2-yl]-1H-pyridin-2-one (267 mg, 0.46 mmol) in THF (2.2 ml) are added cesium carbonate (454 mg, 1.39 mmol) and 2,2,2-trifluoroethanol (2.2) and the reaction mixture is stirred for 2 hours at 80° C. The reaction mixture is filtered over kieselguhr and the filtrate is evaporated. The residue is purified by preparative HPLC to afford 3-[5-(4-methyl-[1,4]diazepan-1-yl)-1H-benzimidazol-2-yl]-5-(1H-pyrrolo[2,3-b]pyridin-4-yl)-1H-pyridin-2-one as orange crystals; HPLC/MS 0.92 min, [M+H]$^+$440. $^1$H NMR (500 MHz, DMSO-d$_6$) δ 12.2 (bs, 3H), 11.84 (s, 1H), 8.96 (d, J=2.7 Hz, 1H), 8.29 (d, J=5.0 Hz, 1H), 8.20 (s, 2H, formate-H), 8.02 (d, J=2.7 Hz, 1H), 7.60 (dd, J=3.5, 2.5 Hz, 1H), 7.47 (d, J=8.8 Hz, 1H), 7.25 (d, J=5.0 Hz, 1H), 6.94 (s, 1H), 6.76 (dd, J=8.9, 2.4 Hz, 1H), 6.65 (dd, J=3.5, 1.8 Hz, 1H), 3.58 (m, 2H), 3.49 (t, J=6.3 Hz, 2H), 2.76 (t, J=4.8 Hz, 2H), 2.58 (t, J=5.4 Hz, 2H), 2.35 (s, 3H), 1.98 (dt, J=11.8, 6.1 Hz, 2H).

The following compounds are prepared analogously

3-[6-(4-Methyl-piperazin-1-yl)-1H-benzimidazol-2-yl]-5-(1H-pyrrolo-[2,3-b]pyridin-4-yl)-1H-pyridin-2-one ("A50")

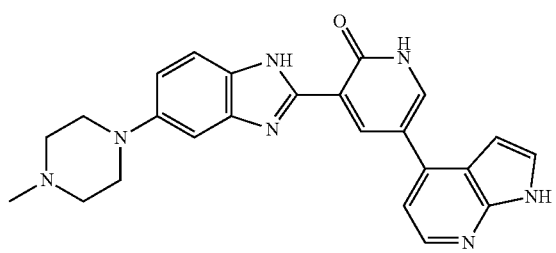 [SMILES: CN1CCN(c2ccc3[nH]c(-c4cc(-c5ccnc6[nH]ccc56)c[nH]c4=O)nc3c2)CC1]

HPLC/MS 0.91 min, [M+H]$^+$426; $^1$H NMR (400 MHz, DMSO-d$_6$, TFA-d$_1$) δ 9.25 (d, J=2.7 Hz, 1H), 8.63 (d, J=6.2 Hz, 1H), 8.55 (d, J=2.6 Hz, 1H), 7.87 (d, J=3.6 Hz, 1H), 7.82 (d, J=6.4 Hz, 1H), 7.80 (d, J=9.3 Hz, 1H), 7.36 (dd, J=9.2, 2.3 Hz, 1H), 7.32 (d, J=2.2 Hz, 1H), 7.17 (d, J=3.6 Hz, 1H), 3.89 (d, J=12.9 Hz, 2H), 3.59 (d, J=11.8 Hz, 2H), 3.25 (m, 2H), 3.15 (t, J=12.1 Hz, 2H), 2.88 (s, 3H).

3-[6-(4-Methyl-piperazin-1-yl)-1H-benzimidazol-2-yl]-5-(1H-pyrrolo[2,3-b]-pyridin-5-yl)-1H-pyridin-2-one ("A51")

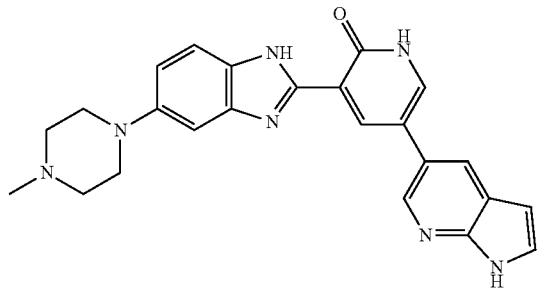 [SMILES: CN1CCN(c2ccc3[nH]c(-c4cc(-c5cnc6[nH]ccc6c5)c[nH]c4=O)nc3c2)CC1]

MS-ESI: [M+H]$^+$426; $^1$H NMR (500 MHz, DMSO-d$_6$, TFA-d$_1$) δ 9.15 (d, J=2.7 Hz, 1H), 8.80 (d, J=2.0 Hz, 1H), 8.77 (d, J=2.0 Hz, 1H), 8.48 (d, J=2.6 Hz, 1H), 7.85 (d, J=9.0 Hz, 1H), 7.79 (d, J=3.4 Hz, 1H), 7.41 (dd, J=9.1, 2.3 Hz, 1H), 7.38 (d, J=2.2 Hz, 1H), 6.80 (d, J=3.5 Hz, 1H), 3.94 (d, J=13.3 Hz, 2H), 3.64 (d, J=12.1 Hz, 2H), 3.29 (m, 2H), 3.20-3.08 (m, 2H), 2.94 (s, 3H).

3-[5-(4-Methyl-piperazin-1-yl)-1H-benzimidazol-2-yl]-5-(2-methyl-1H-pyrrolo-[2,3-b]pyridin-3-yl)-1H-pyridin-2-one ("A52")

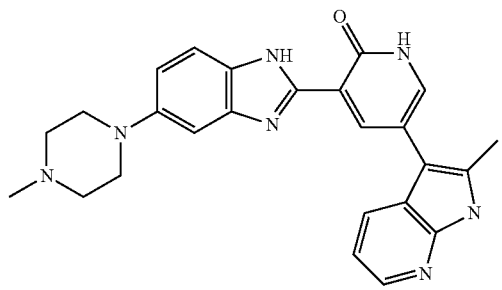

HPLC/MS 0.88 min, [M+H]$^+$440; $^1$H NMR (500 MHz, DMSO-d$_6$, TFA-d$_1$) δ 8.80 (d, J=2.5 Hz, 1H), 8.60 (dd, J=7.9, 1.2 Hz, 1H), 8.50 (dd, J=5.8, 1.2 Hz, 1H), 8.08 (d, J=2.5 Hz, 1H), 7.79 (d, J=9.0 Hz, 1H), 7.55 (dd, J=7.9, 5.8 Hz, 1H), 7.36 (dd, J=9.1, 2.3 Hz, 1H), 7.32 (d, J=2.0 Hz, 1H), 3.88 (d, J=13.3 Hz, 2H), 3.59 (d, J=12.2 Hz, 2H), 3.25 (td, J=12.2, 3.1 Hz, 2H), 3.15-3.04 (m, 2H), 2.90 (s, 3H), 2.59 (s, 3H).

3-[6-(8-Methyl-3,8-diaza-bicyclo[3.2.1]oct-3-yl)-1H-benzimidazol-2-yl]-5-(1H-pyrrolo[2,3-b]pyridin-4-yl)-1H-pyridin-2-one ("A53")

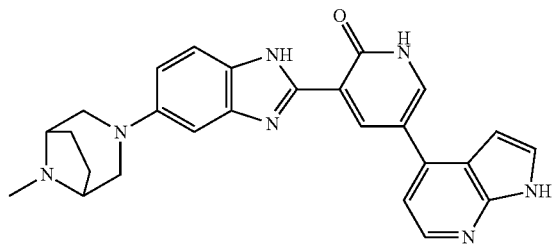 [SMILES: CN1C2CCC1CN(c1ccc3[nH]c(-c4cc(-c5ccnc6[nH]ccc56)c[nH]c4=O)nc3c1)C2]

brown solid, HPLC/MS 0.94 min, [M+H]⁺452; ¹H NMR (400 MHz, DMSO-d₆) δ 9.22 (d, J=2.6 Hz, 1H), 8.66 (d, J=6.3 Hz, 1H), 8.60 (d, J=2.6 Hz, 1H), 7.91 (d, J=3.6 Hz, 1H), 7.83 (m, 2H), 7.36 (d, J=9.3 Hz, 1H), 7.34-7.26 (m, 1H), 7.21 (d, J=3.6 Hz, 1H), 4.17 (s, 2H), 3.84 (d, J=12.5 Hz, 2H), 3.36 (d, J=12.3 Hz, 2H), 2.88 (s, 3H), 2.40-2.27 (m, 2H), 2.15 (d, J=8.8 Hz, 2H).

5-(5-Aminomethyl-1H-benzimidazol-2-yl)-1H-[3,4']bipyridinyl-6-one ("A54") and N-[2-(6-Oxo-1,6-dihydro-[3,4']bipyridinyl-5-yl)-1H-benzimidazol-5-ylmethyl]-acetamide ("A55")

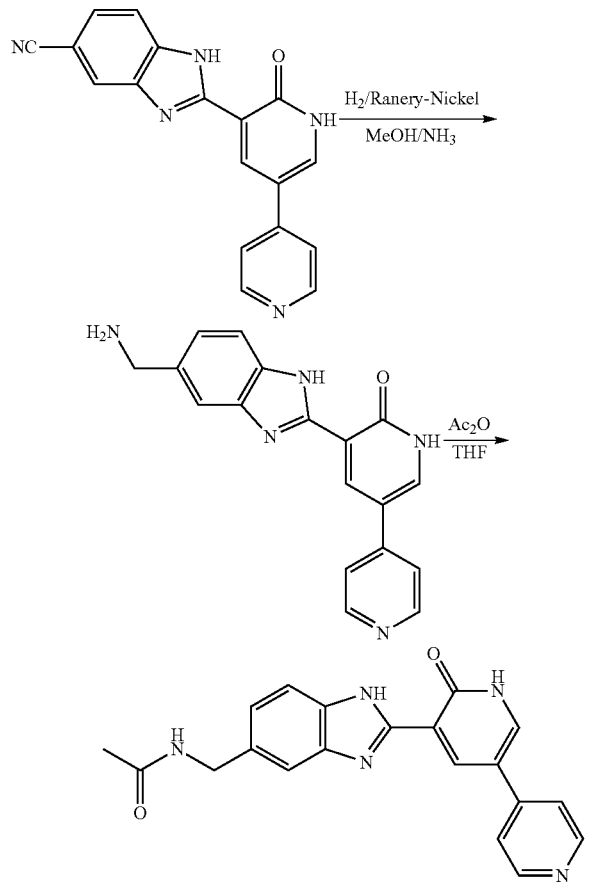

"A54": MS-ESI: [M+H]⁺318; ¹H NMR (400 MHz, DMSO-d₆, TFA-d₁) δ 9.36 (d, J=2.7 Hz, 1H), 9.06 (d, J=7.0 Hz, 2H), 9.01 (d, J=2.7 Hz, 1H), 8.48 (d, J=7.0 Hz, 2H), 8.10-8.00 (m, 2H), 7.71 (dd, J=8.6, 1.6 Hz, 1H), 4.30 (s, 2H).

"A55": MS-ESI: [M+H]⁺360; ¹H NMR (400 MHz, DMSO-d₆, TFA-d₁) δ 9.33 (d, J=2.8 Hz, 1H), 9.06 (d, J=7.0 Hz, 2H), 8.98 (d, J=2.7 Hz, 1H), 8.48 (d, J=7.1 Hz, 2H), 7.92 (d, J=8.5 Hz, 1H), 7.84 (dd, J=1.6, 0.8 Hz, 1H), 7.53 (dd, J=8.6, 1.6 Hz, 1H), 4.48 (s, 2H), 1.95 (s, 3H).

2-(6-Oxo-1,6-dihydro-[3,4']bipyridinyl-5-yl)-3H-benzimidazole-5-carboxylic acid ("A56") and 2-(6-Oxo-1,6-dihydro-[3,4']bipyridinyl-5-yl)-3H-benzimidazole-5-carboxylic acid (2-diethylamino-ethyl)-amide ("A57")

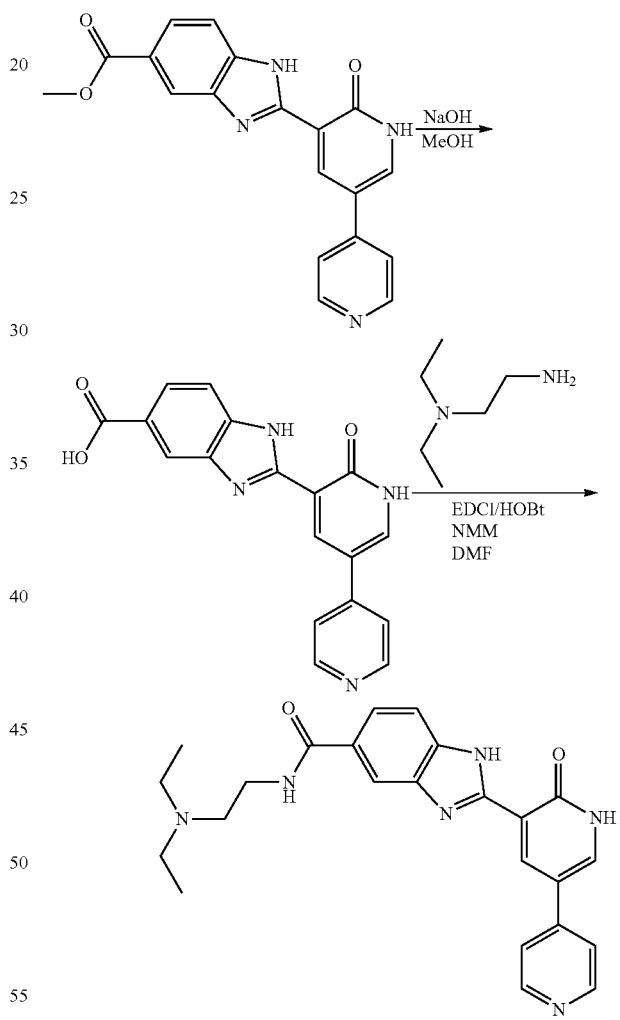

"A56": MS-ESI: [M+H]⁺333; ¹H NMR (400 MHz, DMSO-d₆, TFA-d₁) δ 9.61 (d, J=2.7 Hz, 1H), 9.01 (d, J=7.0 Hz, 2H), 8.98 (d, J=2.7 Hz, 1H), 8.54 (d, J=7.1 Hz, 2H), 8.48 (dd, J=1.5, 0.7 Hz, 1H), 8.13 (dd, J=8.6, 1.5 Hz, 1H), 7.98 (dd, J=8.6, 0.7 Hz, 1H).

"A57": MS-ESI: [M+H]⁺431; ¹H NMR (400 MHz, DMSO-d₆, TFA-d₁) δ 9.41 (d, J=2.7 Hz, 1H), 9.05 (d, J=7.0 Hz, 2H), 9.01 (d, J=2.7 Hz, 1H), 8.50 (d, J=7.2 Hz, 2H), 8.45 (t, J=1.1 Hz, 1H), 8.10 (dd, J=8.7, 1.5 Hz, 1H), 8.07 (dd,

J=8.7, 0.8 Hz, 1H), 3.72 (t, J=6.5 Hz, 2H), 3.35 (t, J=6.6 Hz, 2H), 3.29 (qd, J=7.1, 1.4 Hz, 4H), 1.28 (t, J=7.2 Hz, 6H).

The following compound is prepared analogously:

2-(6-Oxo-1,6-dihydro-[3,4']bipyridinyl-5-yl)-3H-benzimidazole-5-carboxylic acid (1-methyl-piperidin-4-yl)-amide ("A58")

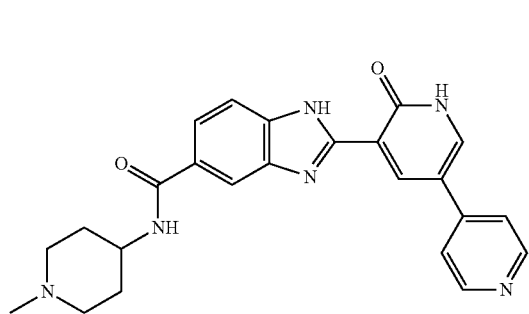 [SMILES: CN1CCC(NC(=O)c2ccc3[nH]c(-c4cc(-c5ccncc5)c[nH]c4=O)nc3c2)CC1]

MS-ESI: [M+H]⁺429.

3-[6-(1-Methyl-piperidin-4-yloxy)-1H-benzimidazol-2-yl]-5-quinolin-4-yl-1H-pyridin-2-one ("A59")

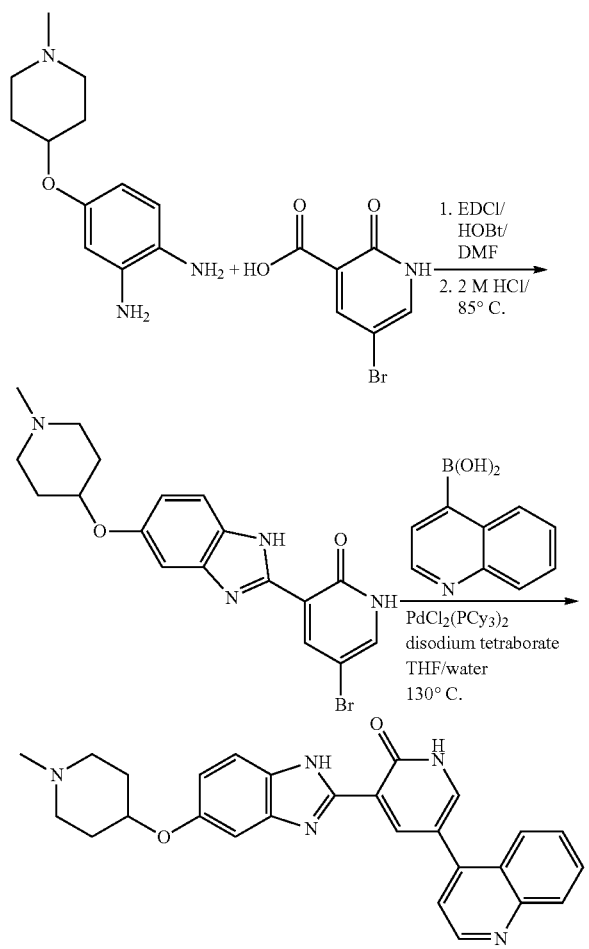

MS-ESI: [M+H]⁺452.

The following compound is prepared analogously:

3-[6-(1-Methyl-piperidin-4-yloxy)-1H-benzimidazol-2-yl]-5-(1H-pyrrolo[2,3-b]-pyridin-4-yl)-1H-pyridin-2-one ("A60")

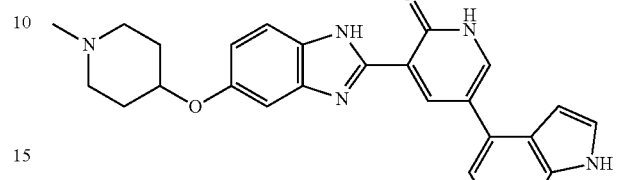

MS-ESI: [M+H]⁺441.

The following examples relate to medicaments:

Example A: Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula I are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula I are introduced into hard gelatine capsules in a conventional manner in such a way that each capsule contains 20 mg of the active ingredient.

Example H: Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. Compounds of the formula I

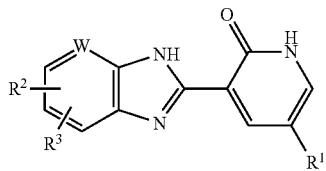

in which
$R^1$ denotes Ar or Het,
$R^2$ denotes H, A, Hal, CN, $NO_2$, $OR^4$, $COOR^4$, $CO(R^4)_2$, $CONR^4[C(R^4)_2]_mN(R^4)_2$, —$[C(R^4)_2]_nNR^4COA$, —$[C(R^4)_2]_nNR^4CO[C(R^4)_2]_nHet^1$, —$[C(R^4)_2]_nN(R^4)_2$, —$[C(R^4)_2]_nHet^1$, $O[C(R^4)_2]_nN(R^4)_2$, $O[C(R^4)_2]_mHet^1$, —$NR^4[C(R^4)_2]_nN(R^4)_2$ or —$NR^4[C(R^4)_2]_nHet^1$,
$R^3$ denotes H, A, Hal or $OR^4$,
$R^4$ denotes H or A',
W denotes CH or N,
A denotes unbranched or branched alkyl having 1-6 C-atoms, in which 1-7 H atoms may be replaced by OH, F, Cl and/or Br and/or in which one or two $CH_2$ groups may be replaced by O, NH, S, SO, $SO_2$ and/or CH=CH groups, or cyclic alkyl having 3-7 C atoms,
A' denotes unbranched or branched alkyl having 1-4 C-atoms,
Ar denotes phenyl or naphthyl, which is unsubstituted or mono-, di- or trisubstituted by Hal, A, $[C(R^4)_2]_nOR^4$ and/or $[C(R^4)_2]_nN(R^4)_2$,
Het denotes pyridyl, quinolyl, [1,8]-naphthyridinyl, pyrazolyl, pyrimidinyl, indolyl, dihydro-indolyl, 1H-pyrrolo[2,3-b]pyridyl, furyl, pyrazolo[1,5-a]pyridinyl or furo[3,2-b]pyridinyl, which may be unsubstituted or mono- or disubstituted by Hal, A, $[C(R^4)_2]_nOR^4$ and/or $[C(R^4)_2]_nN(R^4)_2$,
$Het^1$ denotes piperazinyl, pyridyl, piperidinyl, pyrazolyl, morpholinyl, imidazolyl, 3,8-diaza-bicyclo[3.2.1]octyl, or [1,4]-diazepanyl, which is unsubstituted or mono- or disubstituted by A, $OR^4$, $N(R^4)_2$, Hal and/or =O (carbonyl oxygen),
Hal denotes F, Cl, Br or I,
n denotes 0, 1, 2 or 3,
m denotes 1, 2, 3 or 4,
and pharmaceutically acceptable salts, tautomers and stereoisomers thereof, including mixtures thereof in all ratios.
2. Compounds according to claim 1 in which
$R^2$ denotes H, A, Hal, CN, $OR^4$, $COOR^4$, $CONR^4[C(R^4)_2]_mN(R^4)_2$, —$[C(R^4)_2]_nNR^4COA$, —$[C(R^4)_2]_nNR^4CO[C(R^4)_2]_nHet^1$, —$[C(R^4)_2]_nN(R^4)_2$, —$[C(R^4)_2]_nHet^1$, $O[C(R^4)_2]_mHet^1$ or —$NR^4[C(R^4)_2]_nHet^1$, and pharmaceutically acceptable solvates, salts, tautomers and stereoisomers thereof, including mixtures thereof in all ratios.
3. Compounds according to claim 1, in which
$R^3$ denotes H or $OR^4$,
and pharmaceutically acceptable salts, tautomers and stereoisomers thereof, including mixtures thereof in all ratios.
4. Compounds according to claim 1, in which
W denotes CH,
and pharmaceutically acceptable salts, tautomers and stereoisomers thereof, including mixtures thereof in all ratios.
5. Compounds according to claim 1, in which
A denotes unbranched or branched alkyl having 1-6 C-atoms,
and pharmaceutically acceptable salts, tautomers and stereoisomers thereof, including mixtures thereof in all ratios.
6. Compounds according to claim 1, in which
A' denotes H or methyl,
and pharmaceutically acceptable salts, tautomers and stereoisomers thereof, including mixtures thereof in all ratios.
7. Compounds according to claim 1, in which
Ar denotes phenyl, which is mono-, di- or trisubstituted by Hal, A, $[C(R^4)_2]_nOR^4$ and/or $[C(R^4)_2]_nN(R^4)_2$,
and pharmaceutically acceptable salts, tautomers and stereoisomers thereof, including mixtures thereof in all ratios.
8. Compounds according to claim 1, in which
Het denotes pyridyl, quinolyl, [1,8]-naphthyridinyl, pyrazolyl, pyrimidinyl, indolyl, dihydro-indolyl, 1H-pyrrolo[2,3-b]pyridyl, furyl, pyrazolo[1,5-a]pyridinyl or furo[3,2-b]pyridinyl, which may be unsubstituted or monosubstituted by A,
and pharmaceutically acceptable salts, tautomers and stereoisomers thereof, including mixtures thereof in all ratios.
9. Compounds according to claim 1, in which
$Het^1$ denotes piperazinyl, pyridyl, piperidinyl, pyrazolyl, morpholinyl, imidazolyl, 3,8-diaza-bicyclo[3.2.1]octyl, or [1,4]-diazepanyl, which is unsubstituted or mono- or disubstituted by A, $OR^4$ and/or $N(R^4)_2$,
and pharmaceutically acceptable salts, tautomers and stereoisomers thereof, including mixtures thereof in all ratios.
10. Compounds according to claim 1, in which
$R^1$ denotes Ar or Het,
$R^2$ denotes H, A, Hal, CN, $OR^4$, $COOR^4$, $CONR^4[C(R^4)_2]_mN(R^4)_2$, —$[C(R^4)_2]_nNR^4COA$, —$[C(R^4)_2]_nNR^4CO[C(R^4)_2]_nHet^1$, —$[C(R^4)_2]_nN(R^4)_2$, —$[C(R^4)_2]_nHet^1$, $O[C(R^4)_2]_mHet^1$ or —$NR^4[C(R^4)_2]_nHet^1$,
$R^3$ denotes H or $OR^4$,
$R^4$ denotes H or A',
W denotes CH,
A denotes unbranched or branched alkyl having 1-6 C-atoms,
A' denotes H or methyl,
Ar denotes phenyl, which is mono-, di- or trisubstituted by Hal, A, $[C(R^4)_2]_nOR^4$ and/or $[C(R^4)_2]_nN(R^4)_2$,
Het denotes pyridyl, quinolyl, [1,8]-naphthyridinyl, pyrazolyl, pyrimidinyl, indolyl, dihydro-indolyl, 1H-pyrrolo[2,3-b]pyridyl, furyl, pyrazolo[1,5-a]pyridinyl or furo[3,2-b]pyridinyl, which may be unsubstituted or monosubstituted by A,
$Het^1$ denotes piperazinyl, pyridyl, piperidinyl, pyrazolyl, morpholinyl, imidazolyl, 3,8-diaza-bicyclo[3.2.1]octyl, or [1,4]-diazepanyl, which is unsubstituted or mono- or disubstituted by A, $OR^4$ and/or $N(R^4)_2$,
Hal denotes F, Cl, Br or I,
n denotes 0, 1, 2 or 3,
m denotes 1, 2, 3 or 4, and pharmaceutically acceptable salts, tautomers and stereoisomers thereof, including mixtures thereof in all ratios.

11. Compounds according to claim 1, selected from the group

| No. | Name |
|---|---|
| "A1" | 5-(3-Hydroxymethyl-phenyl)-3-(5-morpholin-4-yl-1H-benzimidazol-2-yl)-1H-pyridin-2-one |
| "A2" | 3-(1H-Benzimidazol-2-yl)-5-quinolin-4-yl-1H-pyridin-2-one |
| "A3" | 5-(5-Chloro-1H-benzimidazol-2-yl)-1H-[3,4']bipyridinyl-6-one |
| "A4" | 5-(5-Methyl-1H-benzimidazol-2-yl)-1H-[3,4']bipyridinyl-6-one |
| "A5" | 5-(4-Methyl-1H-benzimidazol-2-yl)-1H-[3,4']bipyridinyl-6-one |
| "A6" | 5-(5,6-Dimethoxy-1H-benzimidazol-2-yl)-1H-[3,4']bipyridinyl-6-one |
| "A7" | 2-(6-Oxo-1,6-dihydro-[3,4']bipyridinyl-5-yl)-1H-benzimidazole-5-carbonitrile |
| "A8" | Methyl 2-[2-oxo-5-(4-pyridyl)-1H-pyridin-3-yl]-1H-benzimidazole-5-carboxylate |
| "A9" | 3-(6-Morpholin-4-yl-1H-benzimidazol-2-yl)-5-quinolin-4-yl-1H-pyridin-2-one |
| "A10" | 3-[5-(Pyridin-4-yloxy)-1H-benzimidazol-2-yl]-5-quinolin-4-yl-1H-pyridin-2-one |
| "A11" | 5-(2-Chloro-5-hydroxymethyl-phenyl)-3-(5-morpholin-4-yl-1H-benzimidazol-2-yl)-1H-pyridin-2-one |
| "A12" | 5-(3-Hydroxymethyl-phenyl)-3-[5-(4-hydroxy-piperidin-1-yl)-1H-benzimidazol-2-yl]-1H-pyridin-2-one |
| "A13" | 5-(3-Hydroxymethyl-phenyl)-3-(5-piperazin-1-yl-1H-benzimidazol-2-yl)-1H-pyridin-2-one |
| "A14" | 3-(6-Piperazin-1-yl-1H-benzimidazol-2-yl)-5-quinolin-4-yl-1H-pyridin-2-one |
| "A15" | 5-(1H-Indol-3-yl)-3-(6-piperazin-1-yl-1H-benzimidazol-2-yl)-1H-pyridin-2-one |
| "A16" | 5-(4-Hydroxymethyl-phenyl)-3-(5-piperazin-1-yl-1H-benzimidazol-2-yl)-1H-pyridin-2-one |
| "A17" | 3-(5-[1,4]Diazepan-1-yl-1H-benzimidazol-2-yl)-5-(3-hydroxymethyl-phenyl)-1H-pyridin-2-one |
| "A18" | 5-Furo[3,2-b]pyridin-7-yl-3-(5-piperazin-1-yl-1H-benzimidazol-2-yl)-1H-pyridin-2-one |
| "A19" | 5-(3-Methoxymethyl-phenyl)-3-(5-piperazin-1-yl-1H-benzimidazol-2-yl)-1H-pyridin-2-one |
| "A20" | 5-(4-Fluoro-3-hydroxymethyl-phenyl)-3-(5-piperazin-1-yl-1H-benzimidazol-2-yl)-1H-pyridin-2-one |
| "A21" | 5-(3,5-Difluoro-4-hydroxymethyl-phenyl)-3-(5-piperazin-1-yl-1H-benzimidazol-2-yl)-1H-pyridin-2-one |
| "A22" | 5-(2-Chloro-5-hydroxymethyl-phenyl)-3-(5-piperazin-1-yl-1H-benzimidazol-2-yl)-1H-pyridin-2-one dihydrochloride |
| "A23" | 5-(2-Fluoro-3-hydroxymethyl-phenyl)-3-(5-piperazin-1-yl-1H-benzimidazol-2-yl)-1H-pyridin-2-one |
| "A24" | 3-(5-[1,4]Diazepan-1-yl-1H-benzimidazol-2-yl)-5-(4-fluoro-3-hydroxymethyl-phenyl)-1H-pyridin-2-one |
| "A25" | 5-(3-Fluoro-4-hydroxymethyl-phenyl)-3-(5-piperazin-1-yl-1H-benzimidazol-2-yl)-1H-pyridin-2-one |
| "A26" | 3-[5-(4-Amino-piperidin-1-yl)-1H-benzimidazol-2-yl]-5-(3-hydroxymethyl-phenyl)-1H-pyridin-2-one |
| "A27" | 5-(3-Hydroxymethyl-phenyl)-3-[5-(4-methyl-piperazin-1-yl)-1H-benzimidazol-2-yl]-1H-pyridin-2-one |
| "A28" | 5-[5-(4-Methyl-piperazin-1-yl)-1H-benzimidazol-2-yl]-1H-[3,4']bipyridinyl-6-one |
| "A29" | 3-[5-(4-Methyl-piperazin-1-yl)-1H-benzimidazol-2-yl]-5-quinolin-4-yl-1H-pyridin-2-one |
| "A30" | 3-[5-(4-Methyl-piperazin-1-yl)-1H-benzimidazol-2-yl]-5-(1-methyl-1H-pyrazol-4-yl)-1H-pyridin-2-one |
| "A31" | 5-[5-(4-Methyl-piperazin-1-yl)-1H-benzimidazol-2-yl]-1H-[3,3']bipyridinyl-6-one |
| "A32" | 3-[6-(4-Methyl-piperazin-1-yl)-1H-benzimidazol-2-yl]-5-(3-methyl-1H-pyrazol-4-yl)-1H-pyridin-2-on |
| "A33" | 5-(3-Hydroxymethyl-phenyl)-3-[5-(4-methyl-[1,4]diazepan-1-yl)-1H-benzimidazol-2-yl]-1H-pyridin-2-one |
| "A34" | 5-(4-Fluoro-3-hydroxymethyl-phenyl)-3-[5-(4-methyl-piperazin-1-yl)-1H-benzimidazol-2-yl]-1H-pyridin-2-one |
| "A35" | 5-(4-Hydroxymethyl-phenyl)-3-[5-(4-methyl-piperazin-1-yl)-1H-benzimidazol-2-yl]-1H-pyridin-2-one |
| "A36" | 3-[5-(4-Dimethylamino-piperidin-1-yl)-1H-benzimidazol-2-yl]-5-(3-hydroxymethyl-phenyl)-1H-pyridin-2-one |
| "A37" | 5-(2-Fluoro-3-hydroxymethyl-phenyl)-3-[5-(4-methyl-piperazin-1-yl)-1H-benzimidazol-2-yl]-1H-pyridin-2-one |
| "A38" | 3-[5-(4-Hydroxy-piperidin-1-yl)-1H-benzimidazol-2-yl]-5-(1H-pyrrolo[2,3-b]pyridin-4-yl)-1H-pyridin-2-one |
| "A39" | 3-(1H-Benzimidazol-2-yl)-5-(1H-pyrrolo[2,3-b]pyridin-4-yl)-1H-pyridin-2-one |
| "A40" | 3-[5-(Pyridin-4-yloxy)-1H-benzimidazol-2-yl]-5-(1H-pyrrolo[2,3-b]pyridin-4-yl)-1H-pyridin-2-one |

| No. | Name |
|---|---|
| "A41" | 3-(5-Morpholin-4-yl-1H-benzimidazol-2-yl)-5-(1H-pyrrolo-[2,3-b]pyridin-4-yl)-1H-pyridin-2-one |
| "A42" | 3-(5-Methoxy-1H-benzimidazol-2-yl)-5-(1H-pyrrolo[2,3-b]pyridin-4-yl)-1H-pyridin-2-one |
| "A43" | 3-(5-Piperidin-1-yl-1H-benzimidazol-2-yl)-5-(1H-pyrrolo-[2,3-b]pyridin-4-yl)-1H-pyridin-2-one |
| "A44" | 3-(5-Piperazin-1-yl-1H-benzimidazol-2-yl)-5-(1H-pyrrolo-[2,3-b]pyridin-4-yl)-1H-pyridin-2-one |
| "A45" | 5-(2-Methyl-1H-pyrrolo[2,3-b]pyridin-3-yl)-3-(5-piperazin-1-yl-1H-benzimidazol-2-yl)-1H-pyridin-2-one |
| "A46" | 3-[6-(3,8-Diaza-bicyclo[3.2.1]oct-3-yl)-1H-benzimidazol-2-yl]-5-(1H-pyrrolo-[2,3-b]pyridin-4-yl)-1H-pyridin-2-one |
| "A47" | 3-(5-[1,4]Diazepan-1-yl-1H-benzimidazol-2-yl)-5-(1H-pyrrolo[2,3-b]pyridin-4-yl)-1H-pyridin-2-one |
| "A48" | 5-(1H-Indol-4-yl)-3-(5-piperazin-1-yl-1H-benzimidazol-2-yl)-1H-pyridin-2-one |
| "A48a" | 5-(2-Methyl-1H-pyrrolo[2,3-b]pyridin-4-yl)-3-(5-piperazin-1-yl-1H-benzimidazol-2-yl)-1H-pyridin-2-one |
| "A49" | 3-[5-(4-Methyl-[1,4]diazepan-1-yl)-1H-benzimidazol-2-yl]-5-(1H-pyrrolo-[2,3-b]pyridin-4-yl)-1H-pyridin-2-one |
| "A50" | 3-[6-(4-Methyl-piperazin-1-yl)-1H-benzimidazol-2-yl]-5-(1H-pyrrolo-[2,3-b]pyridin-4-yl)-1H-pyridin-2-one |
| "A51" | 3-[6-(4-Methyl-piperazin-1-yl)-1H-benzimidazol-2-yl]-5-(1H-pyrrolo[2,3-b]pyridin-5-yl)-1H-pyridin-2-one |
| "A52" | 3-[5-(4-Methyl-piperazin-1-yl)-1H-benzimidazol-2-yl]-5-(2-methyl-1H-pyrrolo[2,3-b]pyridin-3-yl)-1H-pyridin-2-one |
| "A53" | 3-[6-(8-Methyl-3,8-diaza-bicyclo[3.2.1]oct-3-yl)-1H-benzimidazol-2-yl]-5-(1H-pyrrolo[2,3-b]pyridin-4-yl)-1H-pyridin-2-one |
| "A54" | 5-(5-Aminomethyl-1H-benzimidazol-2-yl)-1H-[3,4']bipyridinyl-6-one |
| "A55" | N-[2-(6-Oxo-1,6-dihydro-[3,4']bipyridinyl-5-yl)-1H-benzimidazol-5-ylmethyl]-acetamide |
| "A56" | 2-(6-Oxo-1,6-dihydro-[3,4']bipyridinyl-5-yl)-3H-benzimidazole-5-carboxylic acid |
| "A57" | 2-(6-Oxo-1,6-dihydro-[3,4']bipyridinyl-5-yl)-3H-benzimidazole-5-carboxylic acid (2-diethylamino-ethyl)-amide |
| "A58" | 2-(6-Oxo-1,6-dihydro-[3,4']bipyridinyl-5-yl)-3H-benzimidazole-5-carboxylic acid (1-methyl-piperidin-4-yl)-amide |
| "A59" | 3-[6-(1-Methyl-piperidin-4-yloxy)-1H-benzimidazol-2-yl]-5-quinolin-4-yl-1H-pyridin-2-one |
| "A60" | 3-[6-(1-Methyl-piperidin-4-yloxy)-1H-benzimidazol-2-yl]-5-(1H-pyrrolo[2,3-b]pyridin-4-yl)-1H-pyridin-2-one | and pharmaceutically acceptable solvates, salts, tautomers and stereoisomers thereof, including mixtures thereof in all ratios.

12. Process for the preparation of compounds of the formula I according to claim 1 and pharmaceutically acceptable salts, solvates, tautomers and stereoisomers thereof, characterised in that a) a compound of the formula II

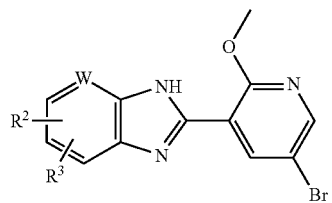

II in which W, $R^2$ and $R^3$ have the meanings indicated in claim 1,
is reacted in a Suzuki-type coupling,
with a compound of formula III

L-$R^1$  III in which $12^1$ has the meanings indicated in claim 1, and L denotes a boronic acid or a boronic acid ester group, to give a compound of formula IV

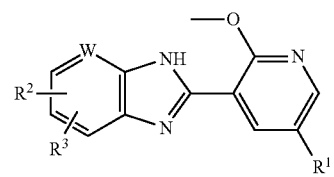

IV in which W, $R^1$, $R^2$ and $R^3$ have the meanings indicated in claim 1,
which subsequently is reacted with a mineral acid,
or b) that it is liberated from one of its functional derivatives by treatment with a solvolysing or hydrolysing agent,
or c) a radical $R^2$ is converted into another radical $R^2$ by acylating or alkylating an amino group,
and/or
a base or acid of the formula I is converted into one of its salts.

13. A pharmaceutical composition comprising at least one compound of the formula I of claim 1 and/or pharmaceutically acceptable salts, solvates, tautomers and stereoisomers thereof, including mixtures thereof in all ratios, and optionally a pharmaceutically acceptable carrier, excipient or vehicle.

14. A method for the treatment of age-related macular degeneration (AMD), choroidal neovascularization (CNV), diabetic retinopathy, diabetic macula edema (DME), fibrodysplasia ossificans progressive, angiogenesis related disorders or bacterial infections, comprising administering a compound of claim 1 to a patient in need thereof.

15. The method for the treatment of diseases selected from cancer of head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors, comprising administering a compound of claim 1 to a patient in need thereof.

16. A pharmaceutical composition comprising at least one compound of the formula I according to claim 1 and/or pharmaceutically acceptable salts, solvates and stereoisomers thereof, including mixtures thereof in all ratios, and at least one further pharmaceutically active ingredient.

17. A pharmaceutical composition in kit form consisting of separate packs of
 (a) an effective amount of a compound of the formula I according to claim 1 and/or pharmaceutically acceptable salts, solvates, salts and stereoisomers thereof, including mixtures thereof in all ratios, and
 (b) an effective amount of a further pharmaceutically active ingredient.

* * * * *